(12) United States Patent
Raval et al.

(10) Patent No.: US 8,420,851 B2
(45) Date of Patent: Apr. 16, 2013

(54) SELECTIVE TR-β 1 AGONIST

(75) Inventors: Saurin Raval, Gujarat (IN); Preeti Raval, Gujarat (IN); Braj Bhushan Lohray, Gujarat (IN); Vidya Bhushan Lohray, Gujarat (IN); Pankaj R. Patel, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 821 days.

(21) Appl. No.: 12/446,820

(22) PCT Filed: Oct. 15, 2007

(86) PCT No.: PCT/IN2007/000493
§ 371 (c)(1),
(2), (4) Date: Oct. 20, 2009

(87) PCT Pub. No.: WO2008/062469
PCT Pub. Date: May 29, 2008

(65) Prior Publication Data
US 2010/0048550 A1    Feb. 25, 2010

(30) Foreign Application Priority Data

Oct. 31, 2006  (IN) .......................... 1813/MUM/2006

(51) Int. Cl.
C07C 229/00 (2006.01)
A61K 9/00 (2006.01)
A01N 25/08 (2006.01)

(52) U.S. Cl.
USPC ................ 560/43; 560/44; 424/400; 424/409

(58) Field of Classification Search ........................ None
See application file for complete search history.

(56) References Cited

U.S. PATENT DOCUMENTS 6,555,580 B2 *  4/2003  Haning et al. ................ 514/563
6,787,652 B1    9/2004  Dow et al.

FOREIGN PATENT DOCUMENTS

| | | |
|---|---|---|
| EP | 1088819 | 4/2001 |
| EP | 1148054 | 10/2001 |
| WO | 2004/067482 | 8/2004 |
| WO | 2004/093799 | 11/2004 |
| WO | 2008/012524 | 1/2008 |

OTHER PUBLICATIONS

<http://www.nlm.nih.gov/medlineplus/cancer.html>), downloaded May 6, 2012.*
National Cancer Institute Fact Sheet 2012, 1-8.*

* cited by examiner

Primary Examiner — Sudhakar Katakam
Assistant Examiner — Clinton Brooks
(74) Attorney, Agent, or Firm — Ladas & Parry LLP

(57) ABSTRACT

The present invention relates to novel compounds of general formula (I) which are thyroid receptor ligands and are preferably selective for the thyroid hormone receptor beta (TR-Beta). Further, the present invention relates to processes of preparing such compounds, their tautomeric forms, novel intermediates involved in their synthesis, their pharmaceutically acceptable salts, methods for using such compounds and pharmaceutical compositions containing them.

10 Claims, No Drawings

SELECTIVE TR-β 1 AGONIST

FIELD OF INVENTION

The present invention relates to novel compounds of general formula (I) which are thyroid receptor (TR) ligands and are preferably selective for the thyroid hormone receptor beta. Further, the present invention relates to processes of preparing such compounds, their tautomeric forms, novel intermediates involved in their synthesis, their pharmaceutically acceptable salts, methods for using such compounds and pharmaceutical compositions containing them.

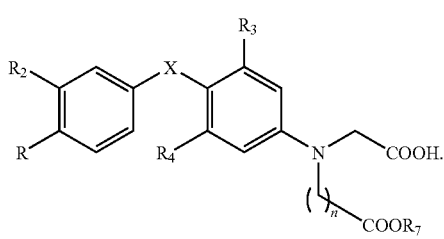

BACKGROUND TO THE INVENTION

Thyroid hormone (Triiodothyronine; T3) is an important endocrine signaling hormone and it is essential for normal development, differentiation and maintenance of metabolic balance in mammals. Natural thyroid hormone, T3 exhibit its physiological effect by acting on a Thyroid Hormone Receptor (THR), which belongs to the nuclear hormone receptor super family. There are two different isoforms of Thyroid Hormone Receptors, THR-α and THR-β. Further these two isoforms are sub-classified as α1; α2 and β1; β2 subtypes. THRβ1 is prevalent in liver (85%), while THR α1 is mainly present in cardiac tissue (Yen P. M., Physiol. Rev; 81 (2001) 1097-1142).

At normal levels, T3 maintains bodyweight, metabolic rate, body temperature, mood and regulate serum cholesterol. Hypothyroidism is associated with weight gain, high levels of low-density lipoproteins (LDL) cholesterol and depression. Hyperthyroidism leads to weight loss, hypermetabolism, lowering of serum LDL levels, cardiac arrhythmia, heart failure, muscle weakness, bone loss and anxiety.

The natural thyroid hormone T3 does not show any selectivity in binding to both of the THR isoforms (THRα1 and THR β1). Thus, administration of T3 lowers plasma cholesterol, low-density lipoprotein (LDL) and triglyceride levels in animal models and humans. However, T3 cannot be used therapeutically to treat hypercholesterolemia and obesity due to its cardiac side effects. However, knockout animal studies as well as results with some selective ligands suggest that such cardiac side effects can be attributed to the THR α1 isoform. Thus some effects of T3 may be therapeutically useful in non-thyroid disorders if adverse effects can be minimized or eliminated. These potentially useful influences include weight reduction, lowering of serum LDL levels, amelioration of depression and stimulation of bone formation (Cheng S., Steroids; 70 (2005); 450-454).

Development of specific and selective thyroid hormone receptor ligands, particularly THR β1 agonist could lead to specific therapies for disorders such as obesity and hyperlipidemia, while avoiding the cardiovascular and other toxicities of native thyroid hormones. Thus, compounds mimicking only the beneficial effects of the thyroid hormone and lacking their cardiac side effects (tachycardia and arrhythmia) potentially could be used to treat a number of conditions such as obesity and dyslipidemia. In this regard, THR agonists that interact selectively with the β1 isoform of the THR offer an especially attractive method for avoiding cardio-toxicity (J. D. Baxter; Trends Endocrinol. Metab., 15 (2004); 154-157).

Various compounds have been disclosed as possible agonists of THR β. Some of the more relevant ones for the present invention includes WO2007039125, WO 0039077, US20040157844 which are incorporated herein as reference.

US20020035153 describes compounds of the following general formula as Thyromimetics.

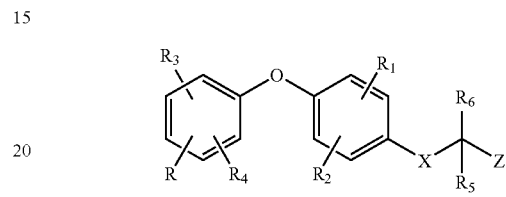

However, none of these compounds have been commercially developed and looking at the beneficial potential and medical need for such compounds, there remains a need for developing further compounds with better therapeutic and/or safety profile. Herein, we disclose novel compounds which shows activity as THR β agonists.

SUMMARY OF THE INVENTION

The present invention describes novel compounds that are thyroid receptor (TR) ligands and are preferably selective for the thyroid hormone receptor beta 1, which are useful for the treatment of a number of conditions such as obesity and dyslipidemia. The novel compounds are defined by the general formula (I) as given below.

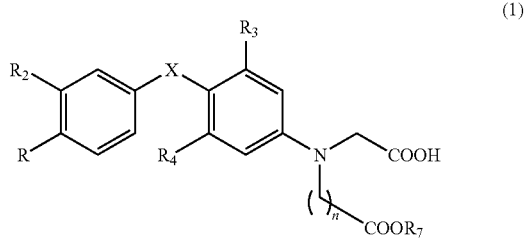

The compounds of the present invention are useful in the treatment of the human or animal body, by regulation of selective thyroid hormone receptor gene expression. The compounds of this invention are therefore suitable for the treatment/mitigation/regulation or prophylaxis of obesity and dyslipidemia.

Preferred Embodiments

The main objective of the present invention is to provide novel compounds of general formula (I), their tautomeric forms, novel intermediates involved in their synthesis, their pharmaceutically acceptable salts, their pharmaceutically acceptable solvates and pharmaceutical compositions containing them or their mixtures suitable for the treatment of obesity and dyslipidemia.

In an embodiment is provided a process for the preparation of novel compounds of general formula (I), their tautomeric forms, novel intermediates involved in their synthesis, their pharmaceutically acceptable salts, pharmaceutically acceptable solvates and pharmaceutical compositions containing them.

In another embodiment is provided pharmaceutical compositions containing compounds of general formula (I), their tautomeric forms, their pharmaceutically acceptable salts, solvates and their mixtures having pharmaceutically acceptable carriers, solvents, diluents, excipients and other media normally employed in their manufacture.

In a further another embodiment is provided the use of the novel compounds of the present invention for the treatment of obesity and dyslipidemia, by administering a therapeutically effective & non-toxic amount of the compound of formula (I), or their pharmaceutically acceptable compositions to the mammals.

DETAILED DESCRIPTION

Accordingly, the present invention relates to compounds of the general formula (I),

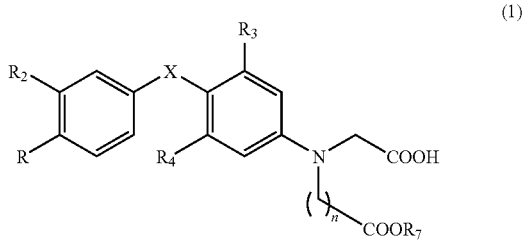

(1)

wherein R=$OR_1$, $NHR_1$ wherein $R_1$ may be selected from H, optionally substituted groups selected from $(C_1-C_6)$alkyl, ar$(C_1-C_6)$alkyl groups; in a preferred embodiment the alkyl groups is selected from $(C_1-C_3)$alkyl and the aryl group represents optionally substituted phenyl group;

$R_2$ represents hydrogen, hydroxyl, halo, acyl, oxo, optionally substituted groups selected from $(C_1-C_6)$alkyl, $(C_3-C_7)$cycloalkyl, aryl, heteroaryl, alkoxy, aryloxy, aralkyl, aralkoxy, carboxylic acid and its derivatives selected from $(C_1-C_3)$alkyl esters and amides, sulfenyl derivatives, sulfonyl derivatives or the groups representing —$CONR_5R_6$, —$SO_2NR_5R_6$, wherein $R_5$ & $R_6$ may be same or different and are independently selected from H, optionally substituted groups selected from $(C_1-C_6)$alkyl, $(C_3-C_7)$cycloalkyl, bicycloalkyl, aryl or the groups $R_5$ & $R_6$ together with the nitrogen atom to which they are attached, form a five to eight membered cyclic ring which may optionally contain one or more hetero atoms selected from N, S, O;

The substituents on $R_2$ may be selected from hydroxy, halo, optionally substituted groups selected from $(C_1-C_6)$alkyl, phenyl, heteroaryl groups;

In a preferred embodiment, the various groups representing $R_2$ may be selected from optionally substituted $(C_1-C_6)$alkyl, acyl, oxo, phenyl, heteroaryl, benzyl, carboxylic acid and its derivatives such as $(C_1-C_3)$alkyl esters and amides, or the groups representing —$CONR_5R_6$, —$SO_2NR_5R_6$, wherein $R_5$ and $R_6$ may be same or different and are independently selected from H, optionally substituted groups selected from $(C_1-C_6)$alkyl, $(C_3-C_7)$cycloalkyl, bicycloalkyl, phenyl or the groups $R_5$ & $R_6$ together with the nitrogen atom to which they are attached, form a five to eight membered cyclic ring which may optionally contain one or more hetero atoms selected from N, O;

$R_3$, $R_4$ may be same or different and are independently selected from H, halogen, optionally substituted $(C_1-C_6)$alkyl groups;

X is selected from O, —$CH_2$—, CO;

'n' represents 0 or 1;

$R_7$ represents H, optionally substituted groups selected from $(C_1-C_6)$alkyl, aryl groups; with the provision that when n=0, $R_7$ does not represent 'H'.

The substituents on alkyl, aryl, heteroaryl or cycloalkyl groups may be selected from hydroxyl, halo, cyano, optionally substituted groups selected from $(C_1-C_6)$alkyl, haloalkyl, alkoxy, oxo, aryl, aryloxy, aralkyl, acyl, alkylthio, thioalkyl groups. When any of these groups are further substituted, the substituents on these substitutes may be selected from those described above.

In a further preferred embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, iso-hexyl and the like;

the "cycloalkyl" or "alicyclic" group used either alone or in combination with other radicals, is selected from a cyclic radical containing three to seven carbons, more preferably cyclopropyl, cyclobutyl, cyclopentyl, cyclohexyl, cycloheptyl and the like;

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "haloalkyl" group is selected from an alkyl radical, as defined above, suitably substituted with one or more halogens; such as perhaloalkyl, more preferably, perfluoro$(C_1-C_6)$alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;

the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "oxo" or "carbonyl" group used either alone (—C═O—) or in combination with other radicals such as alkyl described above, for e.g. "alkylcarbonyl", denotes a carbonyl radical (—C═O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C═O—), wherein the amino group is mono- or di-substituted or unsubstituted, more preferably the groups are selected from methylamide, dimethylamide, ethylamide, diethylamide, and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted;

the "sulfenyl" group or "sulfenyl derivatives" used alone or in combination with other radicals, represents a bivalent group, —SO— or $R_xSO$, where $R_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

Preferred compounds according to the present invention include but not limited to:

{[3,5-Dichloro-4-(4-hydroxy-3-isopropyl-phenoxy)-phenyl]-ethoxycarbonyl-amino}-acetic acid;

{[4-(3-sec-Butyl-4-hydroxy-phenoxy)-3,5-dichloro-phenyl]-ethoxycarbonyl-amino}-acetic acid;

{[4-(3-Benzyl-4-hydroxy-phenoxy)-3,5-dichloro-phenyl]-ethoxycarbonyl-amino}-acetic acid;

({4-[3-(Bicyclo[2.2.1]hept-2-ylcarbamoyl)-4-hydroxy-phenoxy]-3,5-dichloro-phenyl}-ethoxycarbonyl-amino)-acetic acid;

({3,5-Dichloro-4-[4-hydroxy-3-(piperidine-1-carbonyl)-phenoxy]-phenyl}-ethoxycarbonyl-amino)-acetic acid;

{[3,5-Dichloro-4-(3-ethyl-4-hydroxy-phenoxy)-phenyl]-ethoxycarbonyl-amino}-acetic acid;

{[3,5-Dichloro-4-(3-cyclohexylcarbamoyl-4-hydroxy-phenoxy)-phenyl]-ethoxycarbonyl-amino}-acetic acid;

({3,5-Dichloro-4-[4-hydroxy-3-(4-methyl-piperazine-1-carbonyl)-phenoxy]-phenyl}-ethoxycarbonyl-amino)-acetic acid;

{[3,5-Dichloro-4-(3-dimethylcarbamoyl-4-hydroxy-phenoxy)-phenyl]-ethoxycarbonyl-amino}-acetic acid;

{[3,5-Dichloro-4-(3-cyclobutylcarbamoyl-4-hydroxy-phenoxy)-phenyl]-ethoxycarbonyl-amino}-acetic acid;

{[3,5-Dichloro-4-(4-hydroxy-3-propyl-phenoxy)-phenyl]-ethoxycarbonyl-amino}-acetic acid;

{[3,5-Dichloro-4-(4-hydroxy-3-isopropylcarbamoyl-phenoxy)-phenyl]-ethoxycarbonyl-amino}-acetic acid;

{[4-(3-tert-Butyl-4-hydroxy-phenoxy)-3,5-dichloro-phenyl]-ethoxycarbonyl-amino}-acetic acid;

{[3,5-Dichloro-4-(6-hydroxy-biphenyl-3-yloxy)-phenyl]-ethoxycarbonyl-amino}-acetic acid;

({3,5-Dichloro-4-[3-(4-fluoro-benzoyl)-4-hydroxy-phenoxy]-phenyl}-ethoxycarbonyl-amino)-acetic acid;

{[3,5-Dichloro-4-(3-diethylcarbamoyl-4-hydroxy-phenoxy)-phenyl]-ethoxycarbonyl-amino}-acetic acid;

({3,5-Dichloro-4-[3-(5-chloro-thiophene-2-carbonyl)-4-hydroxy-phenoxy]-phenyl}-ethoxycarbonyl-amino)-acetic acid;

{[4-(3-sec-Butyl-4-hydroxy-phenoxy)-3,5-dimethyl-phenyl]-ethoxycarbonyl-amino}-acetic acid;

{[3,5-Dichloro-4-(4-hydroxy-3-phenylcarbamoyl-phenoxy)-phenyl]-ethoxycarbonyl-amino}-acetic acid;

({3,5-Dichloro-4-[3-(4-chloro-benzoyl)-4-hydroxy-phenoxy]-phenyl}-ethoxycarbonyl-amino)-acetic acid;

{[4-(3-sec-Butyl-4-hydroxy-phenoxy)-3,5-dimethyl-phenyl]-carboxymethyl-amino}-acetic acid;

({3,5-Dichloro-4-[3-(2,4-dichloro-benzoyl)-4-hydroxy-phenoxy]-phenyl}-ethoxycarbonyl-amino)-acetic acid;

[[4-(3-sec-Butyl-4-hydroxy-phenoxy)-3,5-dichloro-phenyl]-(4-hydroxy-phenoxycarbonyl)-amino]-acetic acid;

({4-[3-(4-tert-Butyl-benzoyl)-4-hydroxy-phenoxy]-3,5-dichloro-phenyl}-ethoxycarbonyl-amino)-acetic acid;

({3,5-Dichloro-4-[3-(3-chloro-benzoyl)-4-hydroxy-phenoxy]-phenyl}-ethoxycarbonyl-amino)-acetic acid;

{[4-(3-sec-Butyl-4-hydroxy-phenoxy)-3,5-dichloro-phenyl]-carboxymethyl-amino}-acetic acid;

({4-[3-(Bicyclo[2.2.1]hept-2-ylcarbamoyl)-4-hydroxy-phenoxy]-3,5-dichloro-phenyl}-carboxymethyl-amino)-acetic acid;

(Carboxymethyl-{3,5-dichloro-4-[3-(4-chloro-benzoyl)-4-hydroxy-phenoxy]-phenyl}-amino)-acetic acid;

(Carboxymethyl-{3,5-dichloro-4-[4-hydroxy-3-(piperidine-1-carbonyl)-phenoxy]-phenyl}-amino)-acetic acid;

({4-[3-(Bicyclo[2.2.1]hept-2-ylsulfamoyl)-4-hydroxy-phenoxy]-3,5-dichloro-phenyl}-carboxymethyl-amino)-acetic acid;
{Carboxymethyl-[3,5-dichloro-4-(4-hydroxy-3-isopropyl-phenoxy)-phenyl]-amino}-acetic acid;
[[3,5-Dichloro-4-(4-hydroxy-3-isopropyl-phenoxy)-phenyl]-(4-hydroxy-phenoxycarbonyl)-amino]-acetic acid;
(Carboxymethyl-{3,5-dichloro-4-[4-hydroxy-3-(piperidine-1-sulfonyl)-phenoxy]-phenyl}-amino)-acetic acid;
{[4-(3-tert-Butyl-4-hydroxy-phenoxy)-3,5-dichloro-phenyl]-carboxymethyl-amino}-acetic acid;
[[4-(3-tert-Butyl-4-hydroxy-phenoxy)-3,5-dichloro-phenyl]-(4-hydroxy-phenoxycarbonyl)-amino]-acetic acid;
{Carboxymethyl-[3,5-dichloro-4-(3-dimethylcarbamoyl-4-hydroxy-phenoxy)-phenyl]-amino}-acetic acid;
{Carboxymethyl-[4-(4-hydroxy-3-isopropyl-phenoxy)-3,5-dimethyl-phenyl]-amino}-acetic acid;
[[3,5-Dichloro-4-(3-dimethylsulfamoyl-4-hydroxy-phenoxy)-phenyl]-(4-hydroxy-phenoxycarbonyl)-amino]-acetic acid;
[[3,5-Dichloro-4-(3-dimethylcarbamoyl-4-hydroxy-phenoxy)-phenyl]-(4-hydroxy-phenoxycarbonyl)-amino]-acetic acid;
[{3,5-Dichloro-4-[4-hydroxy-3-(piperidine-1-carbonyl)-phenoxy]-phenyl}-(4-hydroxy-phenoxycarbonyl)-amino]-acetic acid;
[{3,5-Dichloro-4-[4-hydroxy-3-(piperidine-1-sulfonyl)-phenoxy]-phenyl}-(4-hydroxy-phenoxycarbonyl)-amino]-acetic acid;
[[4-(4-Hydroxy-3-isopropyl-phenoxy)-3,5-dimethyl-phenyl]-(4-hydroxy-phenoxycarbonyl)-amino]-acetic acid;
[{4-[3-(4-tert-Butyl-benzoyl)-4-hydroxy-phenoxy]-3,5-dichloro-phenyl}-(4-hydroxy-phenoxycarbonyl)-amino]-acetic acid;
[{3,5-Dichloro-4-[3-(4-chloro-benzoyl)-4-hydroxy-phenoxy]-phenyl}-(4-hydroxy-phenoxycarbonyl)-amino]-acetic acid;
[[3,5-Dichloro-4-(4-hydroxy-3-isopropylsulfamoyl-phenoxy)-phenyl]-(4-hydroxy-phenoxycarbonyl)-amino]-acetic acid;
{Carboxymethyl-[3,5-dichloro-4-(3-ethyl-4-hydroxy-phenoxy)-phenyl]-amino}-acetic acid;
[{3,5-Dichloro-4-[3-(3-chloro-benzoyl)-4-hydroxy-phenoxy]-phenyl}-(4-hydroxy-phenoxycarbonyl)-amino]-acetic acid;
[[3,5-Dichloro-4-(3-ethyl-4-hydroxy-phenoxy)-phenyl]-(4-hydroxy-phenoxycarbonyl)-amino]-acetic acid;
[[3,5-Dichloro-4-(6-hydroxy-biphenyl-3-yloxy)-phenyl]-(4-hydroxy-phenoxycarbonyl)-amino]-acetic acid;
[[4-(3-Benzyl-4-hydroxy-phenoxy)-3,5-dichloro-phenyl]-(4-hydroxy-phenoxycarbonyl)-amino]-acetic acid;
[[3,5-Dichloro-4-(3-cyclobutylsulfamoyl-4-hydroxy-phenoxy)-phenyl]-(4-hydroxy-phenoxycarbonyl)-amino]-acetic acid;
[{4-[3-(Bicyclo[2.2.1]hept-2-ylsulfamoyl)-4-hydroxy-phenoxy]-3,5-dichloro-phenyl}-(4-hydroxy-phenoxycarbonyl)-amino]-acetic acid;
[{4-[3-(Bicyclo[2.2.1]hept-2-ylsulfamoyl)-4-hydroxy-phenoxy]-3,5-dibromo-phenyl}-(4-hydroxy-phenoxycarbonyl)-amino]-acetic acid;
[{3,5-Dichloro-4-[4-hydroxy-3-(4-hydroxy-benzoyl)-phenoxy]-phenyl}-(4-hydroxy-phenoxycarbonyl)-amino]-acetic acid;
[{3,5-Dichloro-4-[3-(4-fluoro-benzoyl)-4-hydroxy-phenoxy]-phenyl}-(4-hydroxy-phenoxycarbonyl)-amino]-acetic acid;
[(3,5-Dichloro-4-{3-[(4-chloro-phenyl)-hydroxy-methyl]-4-hydroxy-phenoxy}-phenyl)-(4-hydroxy-phenoxycarbonyl)-amino]-acetic acid;
[{4-[3-(Azepane-1-sulfonyl)-4-hydroxy-phenoxy]-3,5-dichloro-phenyl}-(4-hydroxy-phenoxycarbonyl)-amino]-acetic acid;
({3,5-Dichloro-4-[3-(1-ethyl-propoxy)-4-hydroxy-phenoxy]-phenyl}-ethoxycarbonyl-amino)-acetic acid;
[[4-(3-sec-Butyl-4-hydroxy-phenoxy)-3,5-dimethyl-phenyl]-(4-hydroxy-phenoxycarbonyl)-amino]-acetic acid;
[[3,5-Dichloro-4-(3-cyclohexylsulfamoyl-4-hydroxy-phenoxy)-phenyl]-(4-hydroxy-phenoxycarbonyl)-amino]-acetic acid;
[{3,5-Dichloro-4-[4-hydroxy-3-(morpholine-4-sulfonyl)-phenoxy]-phenyl}-(4-hydroxy-phenoxycarbonyl)-amino]-acetic acid;
({3,5-Dichloro-4-[4-hydroxy-3-(3-methyl-benzoyl)-phenoxy]-phenyl}-ethoxycarbonyl-amino)-acetic acid;
[{3,5-Dichloro-4-[4-hydroxy-3-(pyrrolidine-1-sulfonyl)-phenoxy]-phenyl}-(4-hydroxy-phenoxycarbonyl)-amino]-acetic acid;
{[3,5-Dichloro-4-(4-hydroxy-3-isobutoxy-phenoxy)-phenyl]-ethoxycarbonyl-amino}-acetic acid;
{[3,5-Dichloro-4-(3-cyclohexylmethoxy-4-hydroxy-phenoxy)-phenyl]-ethoxycarbonyl-amino}-acetic acid;
[{3,5-Dichloro-4-[4-hydroxy-3-(3-methyl-benzoyl)-phenoxy]-phenyl}-(4-hydroxy-phenoxycarbonyl)-amino]-acetic acid;
[({3,5-Dibromo-4-[3-(4-chloro-benzoyl)-4-hydroxy-phenoxy]-phenyl}-(4-hydroxy-phenoxycarbonyl)-amino]-acetic acid;
({3,5-Dibromo-4-[3-(4-chloro-benzoyl)-4-hydroxy-phenoxy]-phenyl}-ethoxycarbonyl-amino)-acetic acid;
({3,5-Dichloro-4-[4-hydroxy-3-(4-methyl-benzoyl)-phenoxy]-phenyl-}ethoxycarbonyl-amino)-acetic acid;
[{3,5-Dichloro-4-[4-hydroxy-3-(4-methyl-benzoyl)-phenoxy]-phenyl}-(4-hydroxy-phenoxycarbonyl)-amino]-acetic acid;
{[3,5-Dichloro-4-(3-isopropyl-4-methoxy-phenoxy)-phenyl]-ethoxycarbonyl-amino}-acetic acid ethyl ester;
{[4-(4-Benzyloxy-3-isopropyl-phenoxy)-3,5-dichloro-phenyl]-ethoxycarbonyl-amino}-acetic acid ethyl ester;
{[4-(3-sec-Butyl-4-methoxy-phenoxy)-3,5-dichloro-phenyl]-ethoxycarbonyl-amino}-acetic acid ethyl ester;
{[4-(3-Benzyl-4-methoxy-phenoxy)-3,5-dichloro-phenyl]-ethoxycarbonyl-amino}-acetic acid ethyl ester;
({4-[3-(Bicyclo[2.2.1]hept-2-ylcarbamoyl)-4-methoxy-phenoxy]-3,5-dichloro-phenyl}-ethoxycarbonyl-amino)-acetic acid ethyl ester;
({3,5-Dichloro-4-[4-methoxy-3-(piperidine-1-carbonyl)-phenoxy]-phenyl}-ethoxycarbonyl-amino)-acetic acid ethyl ester;
{[3,5-Dichloro-4-(3-ethyl-4-methoxy-phenoxy)-phenyl]-ethoxycarbonyl-amino}-acetic acid ethyl ester;
{[3,5-Dichloro-4-(3-cyclohexylcarbamoyl-4-methoxy-phenoxy)-phenyl]-ethoxycarbonyl-amino}-acetic acid ethyl ester;
({3,5-Dichloro-4-[4-methoxy-3-(4-methyl-piperazine-1-carbonyl)-phenoxy]-phenyl}-ethoxycarbonyl-amino)-acetic acid ethyl ester;
{[3,5-Dichloro-4-(3-dimethylcarbamoyl-4-methoxy-phenoxy)-phenyl]-ethoxycarbonyl-amino}-acetic acid ethyl ester;
{[3,5-Dichloro-4-(3-cyclobutylcarbamoyl-4-methoxy-phenoxy)-phenyl]-ethoxycarbonyl-amino}-acetic acid ethyl ester;

{[3,5-Dichloro-4-(4-methoxy-3-propyl-phenoxy)-phenyl]-ethoxycarbonyl-amino}-acetic acid ethyl ester;
{[3,5-Dichloro-4-(3-isopropylcarbamoyl-4-methoxy-phenoxy)-phenyl]-ethoxycarbonyl-amino}-acetic acid ethyl ester;
{[4-(3-tert-Butyl-4-methoxy-phenoxy)-3,5-dichloro-phenyl]-ethoxycarbonyl-amino}-acetic acid ethyl ester;
{[3,5-Dichloro-4-(6-methoxy-biphenyl-3-yloxy)-phenyl]-ethoxycarbonyl-amino}-acetic acid ethyl ester;
({3,5-Dichloro-4-[3-(4-fluoro-benzoyl)-4-methoxy-phenoxy]-phenyl}-ethoxycarbonyl-amino)-acetic acid ethyl ester;
{[3,5-Dichloro-4-(3-diethylcarbamoyl-4-methoxy-phenoxy)-phenyl]-ethoxycarbonyl-amino}-acetic acid ethyl ester;
({3,5-Dichloro-4-[3-(5-chloro-thiophene-2-carbonyl)-4-methoxy-phenoxy]-phenyl}-ethoxycarbonyl-amino)-acetic acid ethyl ester;
{[4-(3-sec-Butyl-4-methoxy-phenoxy)-3,5-dimethyl-phenyl]-ethoxycarbonyl-amino}-acetic acid ethyl ester;
{[3,5-Dichloro-4-(4-methoxy-3-phenylcarbamoyl-phenoxy)-phenyl]-ethoxycarbonyl-amino}-acetic acid ethyl ester;
({3,5-Dichloro-4-[3-(4-chloro-benzoyl)-4-methoxy-phenoxy]-phenyl}-ethoxycarbonyl-amino)-acetic acid ethyl ester;
{[4-(3-sec-Butyl-4-methoxy-phenoxy)-3,5-dimethyl-phenyl]-ethoxycarbonylmethyl-amino}-acetic acid ethyl ester;
({3,5-Dichloro-4-[3-(2,4-dichloro-benzoyl)-4-methoxy-phenoxy]-phenyl}-ethoxycarbonyl-amino)-acetic acid ethyl ester;
[[4-(3-sec-Butyl-4-methoxy-phenoxy)-3,5-dichloro-phenyl]-(4-methoxy-phenoxycarbonyl)-amino]-acetic acid ethyl ester;
({4-[3-(4-tert-Butyl-benzoyl)-4-methoxy-phenoxy]-3,5-dichloro-phenyl}-ethoxycarbonyl-amino)-acetic acid ethyl ester;
({3,5-Dichloro-4-[3-(3-chloro-benzoyl)-4-methoxy-phenoxy]-phenyl}-ethoxycarbonyl-amino)-acetic acid ethyl ester;
{[4-(3-sec-Butyl-4-methoxy-phenoxy)-3,5-dichloro-phenyl]-ethoxycarbonylmethyl-amino}-acetic acid ethyl ester;
({4-[3-(Bicyclo[2.2.1]hept-2-ylcarbamoyl)-4-methoxy-phenoxy]-3,5-dichloro-phenyl}-ethoxycarbonylmethyl-amino)-acetic acid ethyl ester;
({3,5-Dichloro-4-[3-(4-chloro-benzoyl)-4-methoxy-phenoxy]-phenyl}-ethoxycarbonylmethyl-amino)-acetic acid ethyl ester;
({3,5-Dichloro-4-[4-methoxy-3-(piperidine-1-carbonyl)-phenoxy]-phenyl}-ethoxycarbonylmethyl-amino)-acetic acid ethyl ester;
({4-[3-(Bicyclo[2.2.1]hept-2-ylsulfamoyl)-4-methoxy-phenoxy]-3,5-dichloro-phenyl}-ethoxycarbonylmethyl-amino)-acetic acid ethyl ester;
{[3,5-Dichloro-4-(3-isopropyl-4-methoxy-phenoxy)-phenyl]-ethoxycarbonylmethyl-amino}-acetic acid ethyl ester;
[[3,5-Dichloro-4-(3-isopropyl-4-methoxy-phenoxy)-phenyl]-(4-methoxy-phenoxycarbonyl)-amino]-acetic acid ethyl ester;
({3,5-Dichloro-4-[4-methoxy-3-(piperidine-1-sulfonyl)-phenoxy]-phenyl}-ethoxycarbonylmethyl-amino)-acetic acid ethyl ester;
{[4-(3-tert-Butyl-4-methoxy-phenoxy)-3,5-dichloro-phenyl]-ethoxycarbonylmethyl-amino}-acetic acid ethyl ester;
[[4-(3-tert-Butyl-4-methoxy-phenoxy)-3,5-dichloro-phenyl]-(4-methoxy-phenoxycarbonyl)-amino]-acetic acid ethyl ester;
{[3,5-Dichloro-4-(3-dimethylcarbamoyl-4-methoxy-phenoxy)-phenyl]-ethoxycarbonylmethyl-amino}-acetic acid ethyl ester;
{Ethoxycarbonylmethyl-[4-(3-isopropyl-4-methoxy-phenoxy)-3,5-dimethyl-phenyl]-amino}-acetic acid ethyl ester;
[[3,5-Dichloro-4-(3-dimethylsulfamoyl-4-methoxy-phenoxy)-phenyl]-(4-methoxy-phenoxycarbonyl)-amino]-acetic acid ethyl ester;
[[3,5-Dichloro-4-(3-dimethylcarbamoyl-4-methoxy-phenoxy)-phenyl]-(4-methoxy-phenoxycarbonyl)-amino]-acetic acid ethyl ester;
[{3,5-Dichloro-4-[4-methoxy-3-(piperidine-1-carbonyl)-phenoxy]-phenyl}-(4-methoxy-phenoxycarbonyl)-amino]-acetic acid ethyl ester;
[{3,5-Dichloro-4-[4-methoxy-3-(piperidine-1-sulfonyl)-phenoxy]-phenyl}-(4-methoxy-phenoxycarbonyl)-amino]-acetic acid ethyl ester;
[[4-(3-Isopropyl-4-methoxy-phenoxy)-3,5-dimethyl-phenyl]-(4-methoxy-phenoxycarbonyl)-amino]-acetic acid ethyl ester;
[{4-[3-(4-tert-Butyl-benzoyl)-4-methoxy-phenoxy]-3,5-dichloro-phenyl}-(4-methoxy-phenoxycarbonyl)-amino]-acetic acid ethyl ester;
[{3,5-Dichloro-4-[3-(4-chloro-benzoyl)-4-methoxy-phenoxy]-phenyl}-(4-methoxy-phenoxycarbonyl)-amino]-acetic acid ethyl ester;
[[3,5-Dichloro-4-(3-isopropylsulfamoyl-4-methoxy-phenoxy)-phenyl]-(4-methoxy-phenoxycarbonyl)-amino]-acetic acid ethyl ester;
{[3,5-Dichloro-4-(3-ethyl-4-methoxy-phenoxy)-phenyl]-ethoxycarbonylmethyl-amino}-acetic acid ethyl ester;
[{3,5-Dichloro-4-[3-(3-chloro-benzoyl)-4-methoxy-phenoxy]-phenyl}-(4-methoxy-phenoxycarbonyl)-amino]-acetic acid ethyl ester;
[[3,5-Dichloro-4-(3-ethyl-4-methoxy-phenoxy)-phenyl]-(4-methoxy-phenoxycarbonyl)-amino]-acetic acid ethyl ester;
[[3,5-Dichloro-4-(6-methoxy-biphenyl-3-yloxy)-phenyl]-(4-methoxy-phenoxycarbonyl)-amino]-acetic acid ethyl ester;
[[4-(3-Benzyl-4-methoxy-phenoxy)-3,5-dichloro-phenyl]-(4-methoxy-phenoxycarbonyl)-amino]-acetic acid ethyl ester;
[[3,5-Dichloro-4-(3-cyclobutylsulfamoyl-4-methoxy-phenoxy)-phenyl]-(4-methoxy-phenoxycarbonyl)-amino]-acetic acid ethyl ester;
[{4-[3-(Bicyclo[2.2.1]hept-2-ylsulfamoyl)-4-methoxy-phenoxy]-3,5-dichloro-phenyl}-(4-methoxy-phenoxycarbonyl)-amino]-acetic acid ethyl ester;
[{4-[3-(Bicyclo[2.2.1]hept-2-ylsulfamoyl)-4-methoxy-phenoxy]-3,5-dibromo-phenyl}-(4-methoxy-phenoxycarbonyl)-amino]-acetic acid ethyl ester;
[{3,5-Dichloro-4-[4-methoxy-3-(4-methoxy-benzoyl)-phenoxy]-phenyl}-(4-methoxy-phenoxycarbonyl)-amino]-acetic acid ethyl ester;
[{3,5-Dichloro-4-[3-(4-fluoro-benzoyl)-4-methoxy-phenoxy]-phenyl}-(4-methoxy-phenoxycarbonyl)-amino]-acetic acid ethyl ester;

[{4-[3-(Azepane-1-sulfonyl)-4-methoxy-phenoxy]-3,5-dichloro-phenyl}-(4-methoxy-phenoxycarbonyl)-amino]-acetic acid ethyl ester;

({4-[4-Benzyloxy-3-(1-ethyl-propoxy)-phenoxy]-3,5-dichloro-phenyl}-ethoxycarbonyl-amino)-acetic acid ethyl ester;

[[4-(3-sec-Butyl-4-methoxy-phenoxy)-3,5-dimethyl-phenyl]-(4-methoxy-phenoxycarbonyl)-amino]-acetic acid ethyl ester;

[[3,5-Dichloro-4-(3-cyclohexylsulfamoyl-4-methoxy-phenoxy)-phenyl]-(4-methoxy-phenoxycarbonyl)-amino]-acetic acid ethyl ester;

[{3,5-Dichloro-4-[4-methoxy-3-(morpholine-4-sulfonyl)-phenoxy]-phenyl}-(4-methoxy-phenoxycarbonyl)-amino]-acetic acid ethyl ester;

({3,5-Dichloro-4-[4-methoxy-3-(3-methyl-benzoyl)-phenoxy]-phenyl}-ethoxycarbonyl-amino)-acetic acid ethyl ester;

[{3,5-Dichloro-4-[4-methoxy-3-(pyrrolidine-1-sulfonyl)-phenoxy]-phenyl}-(4-methoxy-phenoxycarbonyl)-amino]-acetic acid ethyl ester;

{[4-(4-Benzyloxy-3-isobutoxy-phenoxy)-3,5-dichloro-phenyl]-ethoxycarbonyl-amino}-acetic acid ethyl ester;

{[4-(4-Benzyloxy-3-cyclohexylmethoxy-phenoxy)-3,5-dichloro-phenyl]-ethoxycarbonyl-amino}-acetic acid ethyl ester;

[{3,5-Dichloro-4-[4-methoxy-3-(3-methyl-benzoyl)-phenoxy]-phenyl}-(4-methoxy-phenoxycarbonyl)-amino]-acetic acid ethyl ester;

[{3,5-Dibromo-4-[3-(4-chloro-benzoyl)-4-methoxy-phenoxy]-phenyl}-(4-methoxy-phenoxycarbonyl)-amino]-acetic acid ethyl ester;

({3,5-Dibromo-4-[3-(4-chloro-benzoyl)-4-methoxy-phenoxy]-phenyl}-ethoxycarbonyl-amino)-acetic acid ethyl ester;

({3,5-Dichloro-4-[4-methoxy-3-(4-methyl-benzoyl)-phenoxy]-phenyl}-ethoxycarbonyl-amino)-acetic acid ethyl ester;

[{3,5-Dichloro-4-[4-methoxy-3-(4-methyl-benzoyl)-phenoxy]-phenyl}-(4-methoxy-phenoxycarbonyl)-amino]-acetic acid ethyl ester;

The compounds of this invention may be prepared using the reactions and techniques described in the following section. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention. It will also be appreciated that some routine alterations/modifications including requirement of one or more additional steps which may be required for obtaining the compounds of the present invention in preferred yields but are considered to be within the scope of a person skilled in the art, are to be considered to be within the scope of the present invention.

Scheme: 1

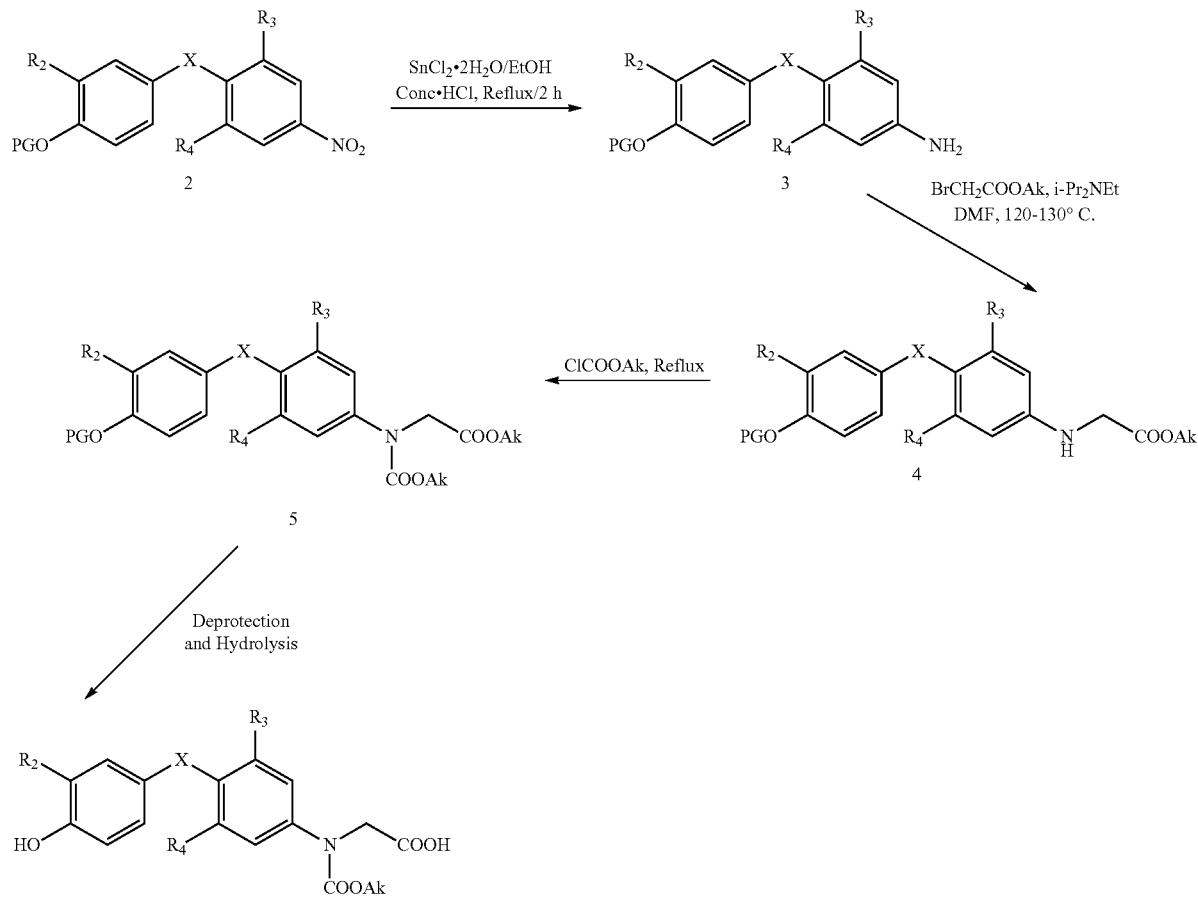

$R_7$ = Alkyl (Ak), n = 0     (I)
'Ak' represents suitable alkyl group

The biaryl ether of formula 2 wherein 'PG' represents suitable protecting groups known to persons skilled in the art (for e.g. those described in T. W. Greene and P. G. M. Wuts "Protective groups in Organic Synthesis", John Wiley & Sons, Inc, 1999, 3$^{rd}$ Ed., 201-245 along with references therein), and all other symbols are as defined elsewhere in the specification, was reduced to give amino compound of formula 3. Reduction may be carried out using suitable reducing agents such as Raney Ni, Pd/C, $SnCl_2.2H_2O$ and the like. This amine 3 may be reacted with suitable alkyl haloacetate in suitable base(s) such as diisopropyl ehtylamine (iPr$_2$-NEt), pyridine, N,N dimethyl aniline or like in solvents selected from DMF,THF and the like or their mixtures to give a compound of formula 4. Further compound of formula 4 was refluxed in suitable alkyl haloformate to give compound of formula 5. Suitable deprotection and hydrolysis of compound of formula 5 gives compound of formula (I)

Scheme: 2

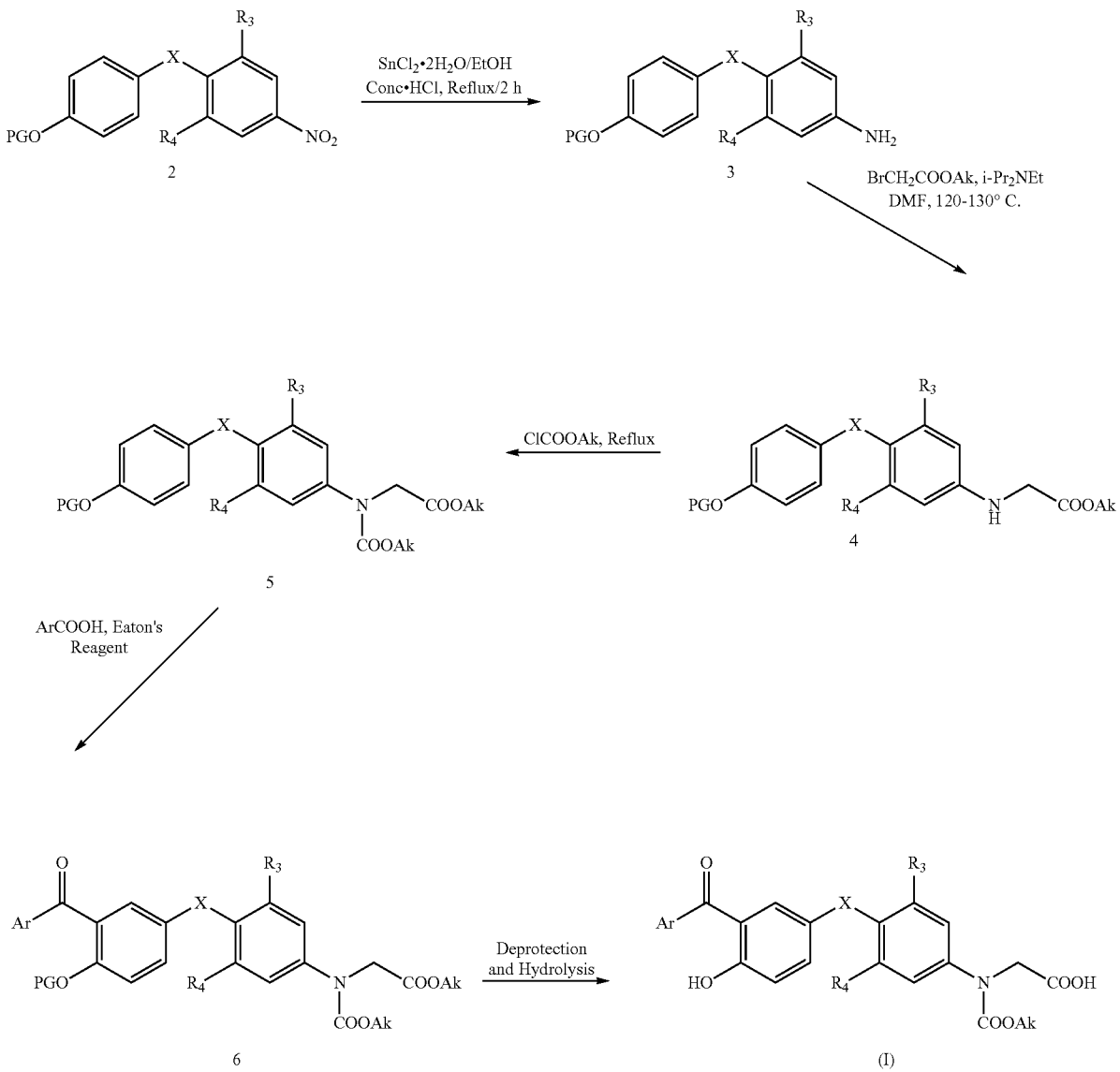

$R_7$ = alkyl, $R_2$ = COAr, n = 0
'Ak' represents suitable alkyl group

The biaryl ether of formula 2 wherein PG represents suitable protecting groups known to persons skilled in the art (for e.g. those described in T. W. Greene and P. G. M. Wuts "Protective groups in Organic Synthesis", John Wiley & Sons, Inc, 1999, 3$^{rd}$ Ed., 201-245 along with references therein), and all other symbols are as defined elsewhere in the specification, was reduced to give amino compound of formula 3. Reduction may be carried out using reducing agents such as Raney Ni, Pd/C, SnCl$_2$.2H$_2$O and the like. This amine 3 may be reacted with suitable alkyl haloacetate in suitable base such as iPr2-NEt, pyridine, N,N dimethyl aniline or like in suitable solvent(s) such as DMF,THF and the like or their mixtures to give a compound of formula 4. Further compound of formula 4 was refluxed in suitable alkyl haloformates to give compound of formula 5. Compound of Formula 5 was reacted with suitable aromatic acids or suitable aromatic acid chloride and appropriate acylating agents to obtain compound of Formula 6. Deprotection and hydrolysis of compound of formula 6, using suitable reagents & techniques as is known in the art, gives compound of formula (I).

Scheme: 3

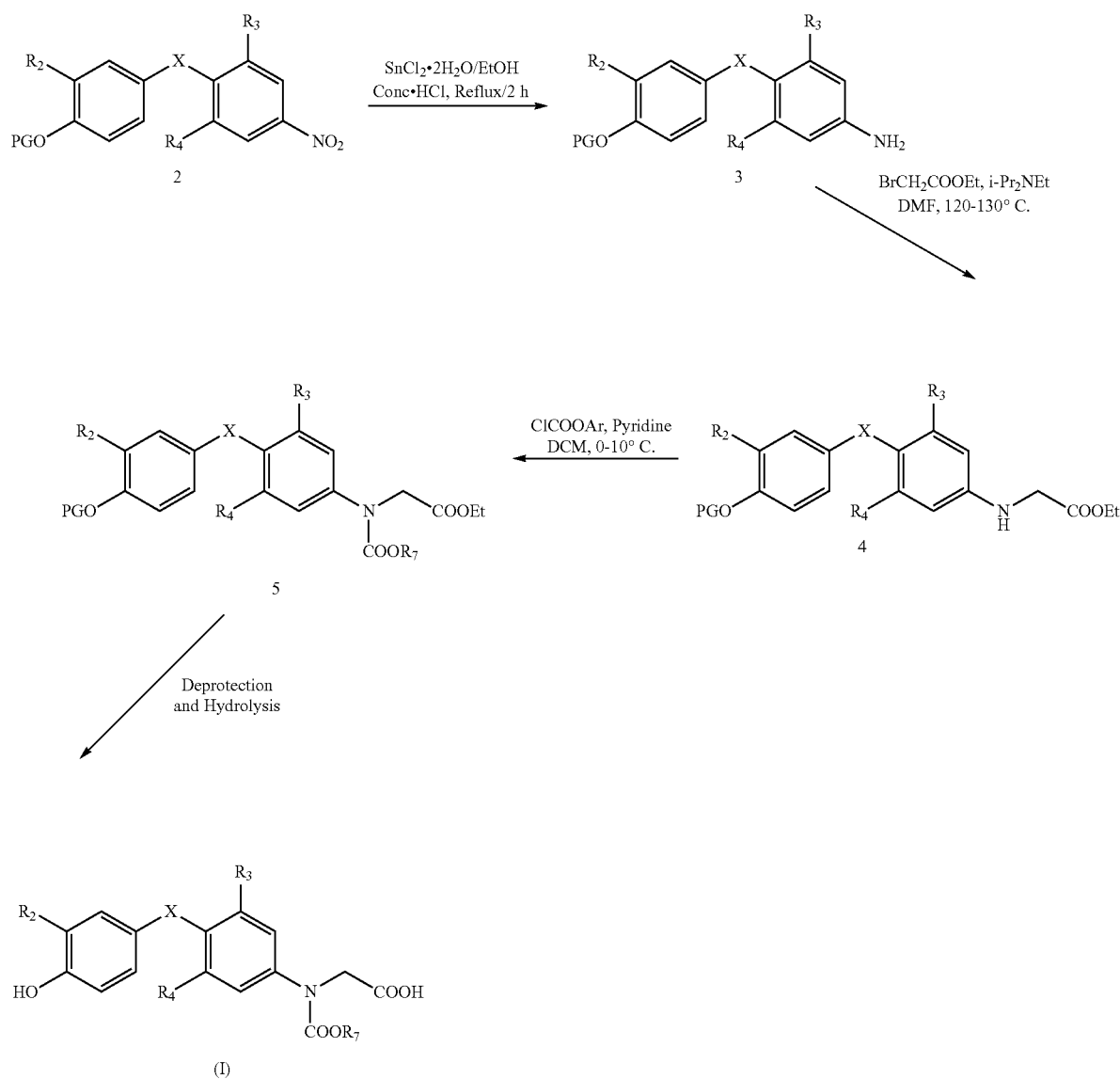

R$_7$ = Aryl, n = 0

The biaryl ether of formula 2 wherein 'PG' represents suitable protecting groups known to persons skilled in the art (for e.g. those described in T. W. Greene and P. G. M. Wuts "Protective groups in Organic Synthesis", John Wiley & Sons, Inc, 1999, 3$^{rd}$ Ed., 201-245 along with references therein), and all other symbols are as defined elsewhere in the specification, was reduced to give amino compound of formula 3. Reduction may be carried out using suitable reducing agents such as Raney Ni, Pd/C, SnCl$_2$.2H$_2$O and the like. This amine 3 may be reacted with suitable alkyl haloacetates in suitable base(s) such as iPr2-NEt, pyridine, N,N dimethyl aniline and the like in suitable solvents such as DMF,THF or their suitable mixtures to give a compound of formula 4 Further compound of formula 4 was reacted with ClCOOAr in suitable base such as pyridine, NEt$_3$ and the like in suitable solvents such as dichloromethane, chloroform and the like or their suitable mixtures to give compound of formula 5. Deprotection and hydrolysis of compound of formula 5 by techniques and reagents known in the art gives compound of formula (I).

Scheme: 4

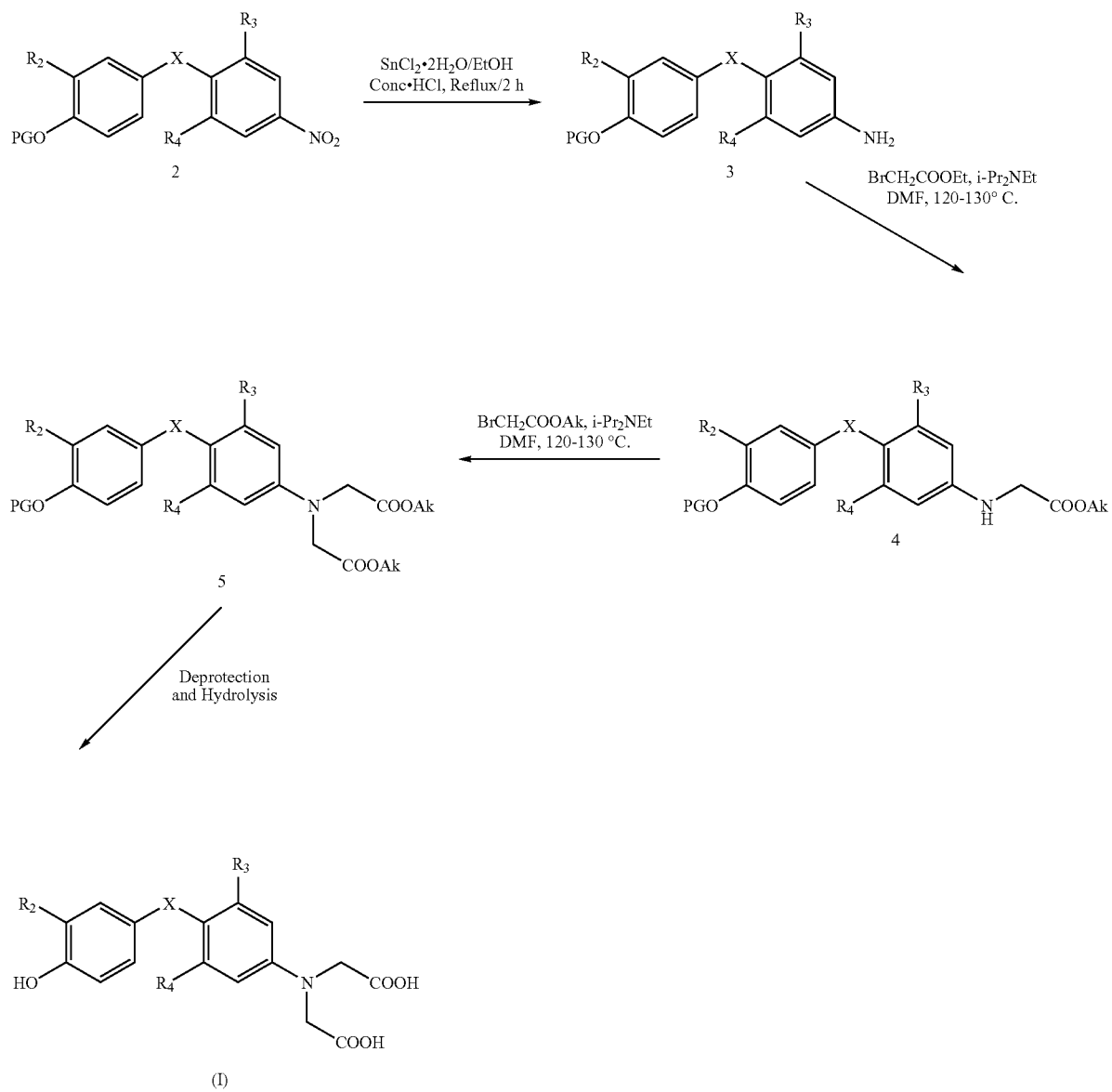

R$_7$ = H, (when 'n' = 1)

The biaryl ether of formula 2 wherein PG represents suitable protecting groups known to persons skilled in the art (for e.g. those described in T. W. Greene and P. G. M. Wuts "Protective groups in Organic Synthesis", John Wiley & Sons, Inc, 1999, $3^{rd}$ Ed., 201-245 along with references therein), and all other symbols are as defined elsewhere in the specification, was reduced to give amino compound of formula 3. Reduction may be carried out using suitable reducing agents such as Raney Ni, Pd/C, $SnCl_2.2H_2O$ and the like. This amine 3 may be reacted with suitable alkyl halo acetates in suitable base such as iPr2-NEt, pyridine, N,N dimethyl aniline and the like in suitable solvents such as DMF,THF and the like to give a compound of formula 4 Again compound of formula 4 was reacted with suitable alkyl halo acetates in suitable base such as iPr2-NEt, pyridine, N,N dimethyl aniline and the like in suitable solvent(s) such as DMF,THF and the like or their suitable mixtures to give a compound of formula 5. Deprotection and hydrolysis of compound of formula 5 by techniques and reagents known in the art gives compound of formula (I)

The invention is explained in greater detail by the examples given below, which are provided by way of illustration only and therefore should not be construed to limit the scope of the invention. As will be clear from the specification, few different sub-classes of compounds within the single general formula (I) have been described. These different subclasses can be prepared by suitable modifications/alterations of one or two of the general processes described in the schemes. Example 2, Example 23, Example 26 and Example 20 each describe in detail processes of preparing compounds of each of the general sub classes. After describing actual processes for preparing compounds of each sub class, characterization data of all the compounds prepared have been provided in random order. However, all the compounds can be prepared by following one of the three processes described earlier with suitable changes as may be specific to the compounds.

1H NMR spectral data given in the examples (vide infra) are recorded using either a 300 MHz spectrometer (Bruker A VANCE-300) or a 400 MHz spectrometer (Bruker Avance2) and reported in δ scale. Until and otherwise mentioned the solvent used for NMR is $CDCl_3$ using tetramethyl silane as the internal standard.

Example 2

Preparation of {[4-(3-sec-Butyl-4-hydroxy-phenoxy)-3,5-dichloro-phenyl]-ethoxycarbonyl-amino}-acetic acid Step 1: Preparation of 4-(3-sec-Butyl-4-methoxy-phenoxy)-3,5-dichloro-phenylamine To a solution of Stannous chloride dihydrate (194.6 g, 0.86 mol) in concentrated HCl (80.0 mL) was added to 3,5-dichloro-4-(4'-methoxy-3-sec-butyl-phenoxy)nitrobenzene (80 g, 0.21 mol) in EtOH (400 mL). The reaction mixture was refluxed for about 2 h. The resulting mixture was brought at 20-30° C. and diluted with ethyl acetate. The mixture was made alkaline with ammonia solution. Resulting solid was filtered through cellite. The organic phase was washed with $H_2O$, brine & dried over sodium sulphate, filtered and concentrated to give 4-(3-sec-Butyl-4-methoxy-phenoxy)-3,5-dichloro-phenylamine (71.8 g; 98% yield).

Step 2: [4-(3-sec-Butyl-4-methoxy-phenoxy)-3,5-dichloro-phenylamino]-acetic acid ethyl ester To 4-(3-sec-Butyl-4-methoxy-phenoxy)-3,5-dichloro-phenylamine (71.8 g, 0.21 mol) was added ethyl bromoacetate (35.26 g, 0.21 mol) and diisopropylethyl amine (27.92 g, 0.21 mol) in DMF (718 mL) were stirred at 120° C. for 18 h. The reaction mixture was poured in to ice-water. The product was taken up in ethyl acetate, washed with $H_2O$, brine & dried over sodium sulphate, filtered and concentrated to give the crude product. The crude product was purified by column chromatography over flash silica gel (Hexane:Ethylacetate 90:10) to afford the pure product [4-(3-sec-Butyl-4-methoxy-phenoxy)-3,5-dichloro-phenylamino]-acetic acid ethyl ester. (48.0 g, 54% yield)

Step 3: {[4-(3-sec-Butyl-4-methoxy-phenoxy)-3,5-dichloro-phenyl]-ethoxycarbonyl-amino}-acetic acid ethyl ester

[4-(3-sec-Butyl-4-methoxy-phenoxy)-3,5-dichloro-phenylamino]-acetic acid ethyl ester (0.9 g, 2.1 mmol) was stirred with ethyl chloroformate (8 mL) at reflux temperature for 16 hrs. From the reaction mixture ethyl chloroformate was evaporated under reduced pressure and the residue was taken up in ethyl acetate, washed with $H_2O$, brine and dried over sodium sulphate, filtered and concentrated to give {[4-(3-sec-butyl-4-methoxy-phenoxy)-3,5-dichloro-phenyl]-ethoxycarbonyl-amino}-acetic acid ethyl ester. (0.8 g, 76% yield)

Step 4: {[4-(3-sec-Butyl-4-hydroxy-phenoxy)-3,5-dichloro-phenyl]-ethoxycarbonyl-amino}-acetic acid A solution of {[4-(3-sec-butyl-4-methoxy-phenoxy)-3,5-dichloro-phenyl]-ethoxycarbonyl-amino}-acetic acid ethyl ester (0.8 g, 1.6 mmol) in $CH_2Cl_2$ (16 mL) was cooled to −60° C. under nitrogen atmosphere. To that 1M $BBr_3$ solution (4.8 mL) was added dropwise. The reaction mixture was allowed to warm up to 20-25° C. over 5 h. then diluted with more $CH_2Cl_2$ (25 mL) and quenched with $H_2O$. After stirring at 20-25° C. for 30 min, organic phase was separated, washed with $H_2O$, brine & dried over sodium sulphate, filtered and concentrated to give crude product. The crude product was purified by column chromatography over flash silica gel (Hexane:Ethylacetate 90:10) to afford the pure product {[4-(3-sec-Butyl-4-hydroxy-phenoxy)-3,5-dichloro-phenyl]-ethoxycarbonyl-amino}-acetic acid ethyl ester (0.77 g, 99% Yield)

The ester (0.77 g, 1.5 mmol) was dissolved in MeOH (18 mL) and to it a solution of NaOH (0.19 g, 4.75 mmol) in $H_2O$ (5.6 mL) was added and it was stirred at 60° C. for 1 hr. Methanol was evaporated from the reaction mixture and $H_2O$ was added, washed with diethyl ether. Aqueous layer was acidified to pH 4 using 10% HCl solution and extracted with ethyl acetate. The organic layer was washed with $H_2O$, brine & dried over sodium sulphate, filtered and concentrated to give 0.75 g of crude product. The crude product was purified by column chromatography (Silica gel, Chloroform Methanol) gradient elution from 95:5 to 90:10 to give pure {[4-(3-sec-Butyl-4-hydroxy-phenoxy)-3,5-dichloro-phenyl]-ethoxycarbonyl-amino}-acetic acid. (0.125 g, 18% yield)

Example 23

Preparation of [[4-(3-sec-Butyl-4-hydroxy-phenoxy)-3,5-dichloro-phenyl]-(4-hydroxy-phenoxycarbonyl)-amino]-acetic acid Step 1: Preparation of [[4-(3-sec-Butyl-4-methoxy-phenoxy)-3,5-dichloro-phenyl]-(4-methoxy-phenoxycarbonyl)-amino]-acetic acid ethyl ester A solution of [4-(3-sec-Butyl-4-methoxy-phenoxy)-3,5-dichloro-phenylamino]-acetic acid ethyl ester (Example 2, step 2) (5.0 g, 0.01 mol) in CH$_2$Cl$_2$ (30 mL) was cooled to 0-5° C. under nitrogen atmosphere. To the solution 4-methoxy phenyl chloroformate (8.75 g, 0.046 mol) in CH$_2$Cl$_2$ (20 mL) was added dropwise. The reaction mixture was allowed to warm up to 20-25° C. over 3 h., diluted further with more CH$_2$Cl$_2$ (25 mL) and quenched with water. After stirring at 20-25° C. for 30 min, organic phase was separated, washed with water, brine, dried over sodium sulphate, filtered and concentrated to give the crude product. The crude product was purified by column chromatography over flash silica gel (hexane: ethyl acetate 90:10) to afford the pure product [[4-(3-sec-Butyl-4-methoxy-phenoxy)-3,5-dichloro-phenyl]-(4-methoxy-phenoxycarbonyl)-amino]-acetic acid ethyl ester (6.4 g, 95% yield)

Step 2: Preparation of [[4-(3-sec-Butyl-4-hydroxy-phenoxy)-3,5-dichloro-phenyl]-(4-hydroxy-phenoxycarbonyl)-amino]-acetic acid To a solution of [[4-(3-sec-Butyl-4-methoxy-phenoxy)-3,5-dichloro-phenyl]-(4-methoxy-phenoxycarbonyl)-amino]-acetic acid ethyl ester (6.4 g, 0.01 mol) in CH$_2$Cl$_2$ (128 mL) was cooled to −60° C. under nitrogen atmosphere. To that 1M BBr$_3$ (boron tribromide) solution (44.44 mL) was added dropwise. The reaction mixture was allowed to warm up to 20-25° C. over 5 h. then diluted with more CH$_2$Cl$_2$ (30 mL) and quenched with H$_2$O. After stirring at 20-25° C. for 30 min, organic phase was separated, washed with H$_2$O, brine & dried over sodium sulphate, filtered and concentrated to give crude product. The crude product was purified by column chromatography over flash silica gel (chloroform:methanol) gradient elution from 95:5 to 90:10 to give pure [[4-(3-sec-Butyl-4-hydroxy-phenoxy)-3,5-dichloro-phenyl]-(4-hydroxy-phenoxycarbonyl)-amino]-acetic acid (3.3 g, 58% yield)

Example 26

Preparation of {[4-(3-sec-Butyl-4-hydroxy-phenoxy)-3,5-dichloro-phenyl]-carboxymethyl-amino}-acetic acid Step 1: Preparation of {[4-(3-sec-Butyl-4-methoxy-phenoxy)-3,5-dichloro-phenyl]-ethoxycarbonylmethyl-amino}-acetic acid ethyl ester To [4-(3-sec-Butyl-4-methoxy-phenoxy)-3,5-dichloro-phenylamino]-acetic acid ethyl ester (Example 2, step 2) (48.0 g, 0.11 mol), ethyl bromoacetate (188 g, 1.12 mol) and diisopropylethylamine (145.57 g, 1.12 mol) in DMF (480 mL) were stirred at 120° C. for 18 h. The reaction mixture was poured in to ice-water. The product was taken up in ethyl acetate, washed with water, brine, dried over sodium sulphate, filtered and concentrated to give the crude product, which was purified by column chromatography over flash silica gel (hexane:ethyl acetate 90:10) to give pure {[4-(3-sec-Butyl-4-methoxy-phenoxy)-3,5-dichloro-phenyl]-ethoxycarbonylmethyl-amino}-acetic acid ethyl ester (27.1 g, 47% yield).

Step 2: Preparation of {[4-(3-sec-Butyl-4-hydroxy-phenoxy)-3,5-dichloro-phenyl]-carboxymethyl-amino}-acetic acid To a solution of {[4-(3-sec-Butyl-4-methoxy-phenoxy)-3,5-dichloro-phenyl]-ethoxycarbonylmethyl-amino}-acetic acid ethyl ester (12.5 g, 0.02 mol) in CH$_2$Cl$_2$ (250 mL) was cooled to −60° C. under nitrogen atmosphere. To that 1M BBr$_3$ solution (122 mL) was added dropwise. The reaction mixture was allowed to warm up to 20-25° C. over 5 h. then diluted with more CH$_2$Cl$_2$ (250 mL) and quenched with H$_2$O. After stirring at 20-25° C. for 30 min, organic phase was separated, washed with water, brine, dried over sodium sulphate, filtered and concentrated to give crude product. The crude product was purified by column chromatography over flash silica gel (chloroform:methanol) gradient elution from 95:5 to 90:10 to give pure {[4-(3-sec-Butyl-4-hydroxy-phenoxy)-3,5-dichloro-phenyl]-carboxymethyl-amino}-acetic acid (6.8 g, 63% yield)

Example 20

Preparation of ({3,5-Dichloro-4-[3-(4-chloro-benzoyl)-4-hydroxy-phenoxy]-phenyl}-ethoxycarbonyl-amino)-acetic acid Step 1:
3,5-Dichloro-4-(4-methoxy-phenoxy)-phenylamine To a solution of stannous chloride dihydrate (32.38 g, 0.14 mol) in concentrated HCl (11 mL) was added 3,5-dichloro-4-(4-methoxy-phenoxy)nitrobenzene (11.3 g, 0.03 mol) in EtOH (56.5 mL). The reaction mixture was refluxed for about 2 h. The resulting mixture was brought at 20-30° C. and diluted with ethyl acetate. The mixture was made alkaline with ammonia solution. Resulting solid was filtered through cellite. The organic phase was washed with water, brine, dried over sodium sulphate, filtered and concentrated to give 3,5-Dichloro-4-(4-methoxy-phenoxy)-phenylamine (10.2 g; % Yield: 99%).

Step 2: [3,5-Dichloro-4-(4-methoxy-phenoxy)-phenylamino]-acetic acid ethyl ester 3,5-Dichloro-4-(4-methoxy-phenoxy)-phenylamine (10.2 g, 0.03 mol), ethyl bromoacetate (5.39 g, 0.03 mol) and diisopropylethylamine (5.1 g, 0.03 mol) in 50 mL of DMF were stirred at 120° C. for 18 h. The reaction mixture was poured in to ice-water. The product was taken up in ethyl acetate, washed with water, brine, dried over sodium sulphate, filtered and concentrated to give the crude product, which was purified by column chromatography over flash silica gel, (hexane: ethyl acetate 90:10) to afford pure [3,5-Dichloro-4-(4-methoxy-phenoxy)-phenylamino]-acetic acid ethyl ester. (10.0 g, 76% yield)

Step 3: {[3,5-Dichloro-4-(4-methoxy-phenoxy)-phenyl]-ethoxycarbonyl-amino}-acetic acid ethyl ester

[3,5-Dichloro-4-(4-methoxy-phenoxy)-phenylamino]-acetic acid ethyl ester (10.0 g, 0.02 mol) was stirred with ethyl chloroformate (95 mL) at reflux temperature for 16 hrs. From the reaction mixture ethyl chloroformate was evaporated under reduced pressure and the residue was taken up in ethyl acetate, washed with water, brine, dried over sodium sulphate, filtered and concentrated to give {[3,5-Dichloro-4-(4-methoxy-phenoxy)-phenyl]-ethoxycarbonyl-amino}-acetic acid ethyl ester (7.25 g, 61% Yield)

Step 4: ({3,5-Dichloro-4-[3-(4-chloro-benzoyl)-4-methoxy-phenoxy]-phenyl}-ethoxycarbonyl-amino)-acetic acid ethyl ester A mixture of {[3,5-Dichloro-4-(4-methoxy-phenoxy)-phenyl]-ethoxycarbonyl-amino}-acetic acid ethyl ester (7.25 g, 0.016 mol) and 4-chlorobenzoic acid (5.13 g, 0.03 mol) in Eaton's reagent (25 mL) was heated at 60° C. for 16 h. The reaction mixture was poured over ice. The product was taken up in ethyl acetate, washed with water, brine, dried over sodium sulphate, filtered and concentrated to give the crude product, which was purified by column chromatography over flash silica gel (hexane:ethylacetate 90:10) to afford pure ({3,5-Dichloro-4-[3-(4-chloro-benzoyl)-4-methoxy-phenoxy]-phenyl}-ethoxycarbonyl-amino)-acetic acid ethyl ester. (3.36 g, 36% yield)

Step 5: Preparation of ({3,5-Dichloro-4-[3-(4-chloro-benzoyl)-4-hydroxy-phenoxy]-phenyl}-ethoxycarbonyl-amino)-acetic acid A solution of {[4-(3-sec-Butyl-4-methoxy-phenoxy)-3,5-dichloro-phenyl]-ethoxycarbonylmethyl-amino}-acetic acid ethyl ester (3.36 g, 5.7 mmol) in $CH_2Cl_2$ (67 mL) was cooled to −60° C. under nitrogen atmosphere. To that 1M $BBr_3$ solution (11.57 mL) was added dropwise. The reaction mixture was stirred at −40 to −60° C. over 0.5 to 1 h. then diluted with more $CH_2Cl_2$ (50 mL) and quenched with $H_2O$. After stirring at 20-25° C. for 30 min, organic phase was separated, washed with water, brine, dried over sodium sulphate, filtered and concentrated. The residue was purified by column chromatography silica gel (hexane:ethyl acetate 90:10) to afford the pure product ({3,5-Dichloro-4-[3-(4-chloro-benzoyl)-4-hydroxy-phenoxy]-phenyl}-ethoxycarbonyl-amino)-acetic acid ethyl ester. (2.27 g, 70% Yield)

The ester (2.27 g, 4.0 mmol) was dissolved in MeOH (14 mL) and to that solution of NaOH (0.48 g, 12 mmol) in $H_2O$ (7 mL) was added and it was stirred at 60° C. for 1 hr. Methanol was evaporated from the reaction mixture and $H_2O$ was added, washed with diethyl ether. The aqueous layer was acidified to pH 4 using 10% HCl solution and extracted with ethyl acetate The organic layer was washed with water, brine, dried over sodium sulphate, filtered and concentrated to give pure product ({3,5-Dichloro-4-[3-(4-chloro-benzoyl)-4-hydroxy-phenoxy]-phenyl}-ethoxycarbonyl-amino)-acetic acid. (1.7 g, 79% yield)

Using appropriate starting materials and suitable modifications of one or more of the processes described above, either alone or in suitable combination of the steps disclosed therein, including suitable addition and/or deletion of steps as may be necessary, well within the scope of a person skilled in the art, the following compounds were prepared in an analogous manner.

Example 1

{[3,5-Dichloro-4-(4-hydroxy-3-isopropyl-phenoxy)-phenyl]-ethoxycarbonyl-amino}-acetic acid $^1$H NMR: ($CDCl_3$, 300 MHz): 1.22-1.25 (9H, m), 3.18 (1H, m), 4.22-4.24 (2H, m), 4.37 (2H, s) 6.39 (1H, m), 6.61-6.64 (1H, d, J=8.7 Hz), 6.85 (1H, s), 7.39 (2H, s)
% Yield: 18%

Example 2

{[4-(3-sec-Butyl-4-hydroxy-phenoxy)-3,5-dichloro-phenyl]-ethoxycarbonyl-amino}-acetic acid $^1$H NMR: ($CDCl_3$, 300 MHz): 0.86 (3H, t, J=7.35Hz), 1.21 (3H, d, J=6.9 Hz), 1.22-1.26 (2H, m), 1.55-1.57 (3H, m), 2.89-2.94 (1H, m), 4.22-4.24 (2H, m), 4.38 (2H, s), 6.40-6.41 (1H, m), 6.64 (1H, d, J=9 Hz), 6.78 (1H, d, J=2.88 Hz), 7.38 (2H, s)
% Yield: 18%

Example 3

{[4-(3-Benzyl-4-hydroxy-phenoxy)-3,5-dichloro-phenyl]-ethoxycarbonyl-amino}-acetic acid 1H NMR: (DMSO-D6, 300 MHz): 1.15 (3H, t, J=7.05 Hz), 3.82 (2H, s), 4.11 (4H, m), 6.61 (1H, m), 6.70 (1H, m), 6.73 (1H, m), 7.18-7.25 (5H, m), 7.54 (2H, s)
% Yield: 25%

Example 4

({4-[3-(Bicyclo[2.2.1]hept-2-ylcarbamoyl)-4-hydroxy-phenoxy]-3,5-dichloro-phenyl}-ethoxycarbonyl-amino)-acetic acid $^1$H NMR: (DMSO-D6, 300 MHz): 1.15-1.19 (7H, m), 1.47-1.71 (4H, m), 2.21-2.26 (2H, m), 3.72 (1H, bs), 4.09-4.16 (2H, q, J=6.96 Hz & 7.02 Hz), 4.34 (2H, s), 6.68-6.72 (1H, dd, J=2.94 Hz & 8.94 Hz), 6.85 (1H, d, J=8.94 Hz), 7.58 (2H, s), 7.66 (1H, d, J=2.85 Hz)
% Yield: 86%

Example 5

({3,5-Dichloro-4-[4-hydroxy-3-(piperidine-1-carbonyl)-phenoxy]-phenyl}-ethoxycarbonyl-amino)-acetic acid $^1$H NMR: (DMSO-D6, 300 MHz): 1.15 (3H, t, J=7 Hz), 1.43 (4H, m), 1.54 (2H, m), 3.14 (4H, m), 4.06-4.14 (2H, m), 4.34 (2H, s), 6.46 (1H, d, J=2.94 Hz), 6.72-6.83 (2H, m), 7.55 (2H, s)
% Yield: 80%

Example 6

{[3,5-Dichloro-4-(3-ethyl-4-hydroxy-phenoxy)-phenyl]-ethoxycarbonyl-amino}-acetic acid $^1$H NMR: (DMSO-D6, 300 MHz): 1.07 (3H, t, J=7.47 Hz), 1.15 (3H, t, J=7.02 Hz), 2.48-2.52 (2H, m), 4.06-4.13 (2H, q, J=6.87 Hz & 7.02 Hz), 4.31 (2H, s), 6.32-6.36 (1H, dd, J=3.15 Hz & 8.79 Hz), 6.62 (1H, d, J=3Hz), 6.67 (1H, d, J=8.7Hz), 7.54 (2H, s)
% Yield: 38%

Example 7

{[3,5-Dichloro-4-(3-cyclohexylcarbamoyl-4-hydroxy-phenoxy)-phenyl]-ethoxycarbonyl-amino}-acetic acid $^1$H NMR: (DMSO-D6, 300 MHz): 1.16 (3H, t, J=6.9 Hz), 1.2-1.3 (6H, m), 1.5-1.6 (4H, m), 3.78 (1H, m), 4.07-4.14 (2H, q, J=6.93 Hz & 6.99 Hz), 4.30 (2H, s), 6.69-6.73 (1H, dd, J=3.03 Hz & 9.06 Hz), 6.85 (1H, d, J=9 Hz), 7.57 (3H, s)
% Yield: 39%

Example 8

({3,5-Dichloro-4-[4-hydroxy-3-(4-methyl-piperazine-1-carbonyl)-phenoxy]-phenyl}-ethoxycarbonyl-amino)-acetic acid ¹H NMR: (CD₃OD, 300 MHz): 1.23 (3H, t, J=7.67 Hz), 2.92 (3H, s), 3.29 (4H, m), 3.71 (4H, m), 4.16-4.23 (2H, q, J=6.78 Hz & 7.02 Hz), 4.35 (2H, s), 6.71 (1H, m), 6.85 (2H, m), 7.52 (2H, s)
% Yield: 59%

Example 9

{[3,5-Dichloro-4-(3-dimethylcarbamoyl-4-hydroxy-phenoxy)-phenyl]-ethoxycarbonyl-amino}-acetic acid ¹H NMR: (CD₃OD, 300 MHz): 1.25 (3H, m), 2.97 (6H, s), 4.18-4.20 (2H, m), 4.35 (2H, s), 6.6 (1H, m), 6.8 (2H, m), 7.51 (2H, s)
% Yield: 77%

Example 10

{[3,5-Dichloro-4-(3-cyclobutylcarbamoyl-4-hydroxy-phenoxy)-phenyl]-ethoxycarbonyl-amino}-acetic acid ¹H NMR: (DMSO-D6, 300 MHz): 1.16 (3H, t, J=7Hz), 1.67-1.69 (2H, m), 2.03-2.09 (2H, m), 2.20 (2H, m), 3.14 (1H, m), 4.07-4.14 (2H, q, J=6.7 Hz & 6.7 Hz), 4.33 (2H, s), 6.72-6.75 (1H, m), 6.85 (1H, d, J=9Hz), 7.57 (3H, m)
% Yield: 72%

Example 11

{[3,5-Dichloro-4-(4-hydroxy-3-propyl-phenoxy)-phenyl]-ethoxy-carbonyl-amino}-acetic acid ¹H NMR: (DMSO-D6, 300 MHz): 0.85 (3H, t, J=7.33 Hz), 1.15 (3H, t, J=7.02 Hz), 1.47-1.49 (2H, m), 2.48-2.49 (2H, m), 4.07-4.09 (2H, m), 4.17 (2H, s), 6.37-6.40 (1H, m), 6.56 (1H, d, J=3 Hz), 6.68 (1H, d, J=8.79 Hz), 7.55 (2H, s)
% Yield: 10%

Example 12

{[3,5-Dichloro-4-(4-hydroxy-3-isopropylcarbamoyl-phenoxy)-phenyl]-ethoxycarbonyl-amino}-acetic acid ¹H NMR: (DMSO-D6, 300 MHz): 1.14-1.22 (9H, m), 2.52 (1H, m), 4.07-4.14 (2H, m), 4.34 (2H, s), 6.69-6.73 (1H, dd, J=3Hz & 8.94 Hz), 6.84 (1H, d, J=9 Hz), 7.57 (2H, s), 7.60 (1H, d, J=3.06 Hz)
% Yield: 74%

Example 13

{[4-(3-tert-Butyl-4-hydroxy-phenoxy)-3,5-dichloro-phenyl]-ethoxycarbonyl-amino}-acetic acid ¹H NMR: (DMSO-D6, 300 MHz): 1.15 (3H, t, J=6.90 Hz), 1.29 (9H, s), 4.06-4.13 (2H, q, J=6.87 Hz & 6.99 Hz), 4.28 (2H, s), 6.29 (1H, d, J=5.99 Hz), 6.66 (1H, d, J=8.71 Hz), 6.73 (1H, m), 7.54 (2H, s)
% Yield: 25%

Example 14

{[3,5-Dichloro-4-(6-hydroxy-biphenyl-3-yloxy)-phenyl]-ethoxycarbonyl-amino}-acetic acid ¹H NMR: (DMSO-D6, 300 MHz): 1.14 (3H, t, J=7Hz), 4.05-4.12 (2H, q, J=6.93 Hz & 7.14 Hz), 4.22 (2H, s), 6.60-6.64 (1H, dd, J=3.3 Hz & 8.7 Hz), 6.70 (1H, d, J=2.8 Hz), 6.89 (1H, d, J=8.7 Hz), 7.28-7.30 (1H, m), 7.34-7.39 (2H, m), 7.46-7.48 (2H, m), 7.56 (2H, s)
% Yield: 20%

Example 15

({3,5-Dichloro-4-[3-(4-fluoro-benzoyl)-4-hydroxy-phenoxy]-phenyl}-ethoxycarbonyl-amino)-acetic acid ¹H NMR: (DMSO-D6, 300 MHz): 1.11 (3H, t, J=6.04 Hz), 4.05-4.12 (2H, q, J=7.11 Hz & 7.11 Hz), 4.23 (2H, s), 6.72 (1H, m), 6.94 (2H, m), 7.30-7.35 (2H, m), 7.56 (2H, s), 7.73-7.78 (2H, m)
% Yield: 81%

Example 16

{[3,5-Dichloro-4-(3-diethylcarbamoyl-4-hydroxy-phenoxy)-phenyl]-ethoxycarbonyl-amino}-acetic acid ¹H NMR: (CDCl₃, 300 MHz): 1.15 (6H, t, J=6.99 Hz), 1.26 (3H, m), 3.40-3.49 (4H, m), 4.21-4.24 (2H, q, J=7.14 Hz & 7.14 Hz), 4.37 (2H, s), 6.60 (1H, m), 6.95-6.98 (2H, m), 7.40 (2H, s)
% Yield: 87%

Example 17

({3,5-Dichloro-4-[3-(5-chloro-thiophene-2-carbonyl)-4-hydroxy-phenoxy]-phenyl}-ethoxycarbonyl-amino)-acetic acid ¹H NMR: (DMSO-D6, 300 MHz): 1.13 (3H, t, J=6.7 Hz), 4.03-4.10 (2H, q, J=6.96 Hz & 7.23 Hz), 4.13 (2H, s), 6.76 (1H, d, J=2.4 Hz), 6.89-6.97 (2H, m), 7.25 (1H, d, J=3.9 Hz), 7.38 (1H, d, J=4.2 Hz), 7.57 (2H, s)
% Yield: 81%

Example 18

{[4-(3-sec-Butyl-4-hydroxy-phenoxy)-3,5-dimethyl-phenyl]-ethoxycarbonyl-amino}-acetic acid ¹H NMR: (DMSO-D6, 300 MHz): 0.74 (3H, t, J=7.2 Hz), 1.06 (3H, d, J=6.8 Hz), 1.13-1.18 (3H, m), 1.41-1.49 (2H, m), 2.00 (6H, s), 2.71-2.95 (1H, m), 4.00-4.05 (2H, m), 4.18 (2H, s), 6.22 (1H, d, J=6.3 Hz), 6.54 (1H, m), 6.64 (1H, d, J=8.7 Hz), 7.04 (2H, s)
% Yield: 90%

Example 19

{[3,5-Dichloro-4-(4-hydroxy-3-phenylcarbamoyl-phenoxy)-phenyl]-ethoxycarbonyl-amino}-acetic acid ¹H NMR: (CDCl₃, 300 MHz): 1.28 (3H, t, J=7.17 Hz), 4.21-4.25 (2H, m), 4.39 (2H, s), 6.91-6.98 (1H, m), 7.13 (1H, m), 7.21-7.26 (2H, m), 7.37-7.42 (4H, m), 7.55-7.57 (2H, d, J=7.8 Hz)
% Yield: 91%

Example 20

({3,5-Dichloro-4-[3-(4-chloro-benzoyl)-4-hydroxy-phenoxy]-phenyl}-ethoxycarbonyl-amino)-acetic acid ¹H NMR: (CDCl₃, 300 MHz): 1.25-1.33 (3H, m), 4.21-4.24 (2H, m), 4.36 (2H, s), 7.01-7.08 (3H, m), 7.38 (2H, m), 7.46 (2H, d, J=8.43 Hz), 7.63 (2H, d, J=8.43 Hz)
% Yield: 79%

Example 21

{[4-(3-sec-Butyl-4-hydroxy-phenoxy)-3,5-dimethyl-phenyl]-carboxymethyl-amino}-acetic acid ¹H NMR: (DMSO-D6, 300 MHz): 0.75 (3H, t, J=7.2 Hz), 1.06 (3H, d, J=6.6 Hz), 1.13-1.44 (2H, m), 1.96 (6H, d, J=8.7 Hz), 2.84-2.91 (1H, m), 4.01 (4H, s), 6.15-6.21 (3H, m), 6.45-6.62 (2H, m)
% Yield: 75%

Example 22

({3,5-Dichloro-4-[3-(2,4-dichloro-benzoyl)-4-hydroxy-phenoxy]-phenyl}-ethoxycarbonyl-amino)-acetic acid ¹NMR: (CDCl₃, 300 MHz): 1.25-1.28 (3H, m), 4.22-4.25 (2H, m), 4.36 (2H, s), 6.78 (1H, m), 7.00 (2H, m), 7.32-7.36 (3H, m), 7.49 (2H, s)
% Yield: 15%

Example 23

[[4-(3-sec-Butyl-4-hydroxy-phenoxy)-3,5-dichloro-phenyl]-(4-hydroxy-phenoxycarbonyl)-amino]-acetic acid ¹H NMR: (DMSO-D6, 300 MHz): 0.75 (3H, t, J=7.2 Hz), 1.07 (3H, d, J=6.9 Hz), 1.40-1.53 (2H, m), 2.89-2.96 (1H, m), 4.44 (2H, s), 6.29-6.32 (1H, dd, J=3.3 Hz & 8.7 Hz), 6.57 (2H, d, J=8.7 Hz), 6.65 (2H, d, J=3.3 Hz), 6.92 (2H, d, J=9 Hz), 7.82 (2H, s)
% Yield: 58%

Example 24

({4-[3-(4-tert-Butyl-benzoyl)-4-hydroxy-phenoxy]-3,5-dichloro-phenyl}-ethoxycarbonyl-amino)-acetic acid ¹H NMR: (CDCl₃, 300 MHz): 1.25 (3H, m), 1.36 (9H, s), 4.21-4.24 (2H, m), 4.35 (2H, s), 6.97-7.02 (3H, m), 7.37 (2H, s), 7.51 (2H, d, J=8.31 Hz), 7.66 (2H, d, J=8.28 Hz)
% Yield: 64%

Example 25

({3,5-Dichloro-4-[3-(3-chloro-benzoyl)-4-hydroxy-phenoxy]-phenyl}-ethoxycarbonyl-amino)-acetic acid ¹H NMR: (DMSO-D6, 300 MHz): 1.14 (3H, t, J=7.02 Hz), 4.06-4.13 (2H, q, J=6.87 Hz & 6.99 Hz), 4.32 (2H, s), 6.75 (1H, m), 6.94-7.02 (2H, m), 7.53 (3H, m), 7.61 (2H, d, J=7.17 Hz), 7.69 (1H, d, J=7.59 Hz)
% Yield: 43%

Example 26

{[4-(3-sec-Butyl-4-hydroxy-phenoxy)-3,5-dichloro-phenyl]-carboxymethyl-amino}-acetic acid ¹H NMR: (DMSO-D6, 300 MHz): 0.76 (3H, t, J=7.23 Hz), 1.07 (3H, d, J=6.9 Hz), 1.45-1.52 (2H, m), 2.90-2.92 (1H, m), 3.98 (4H, bs), 6.22 (1H, m), 6.45 (2H, s), 6.62-6.65 (2H, m)
% Yield: 63%

Example 27

({4-[3-(Bicyclo[2.2.1]hept-2-ylcarbamoyl)-4-hydroxy-phenoxy]-3,5-dichloro-phenyl}-carboxymethyl-amino)-acetic acid ¹H NMR: (DMSO-D6, 300 MHz): 1.10-1.21 (4H, m), 1.46 (4H, d, J=7.5 Hz), 2.21 (2H, d), 3.70 (1H, m), 4.11 (4H, s), 6.62 (2H, d, J=4 Hz), 6.81 (1H, d, J=9 Hz), 7.60 (1H, d, J=2.7 Hz), 8.43 (1H, d, J=8.8 Hz)
% Yield: 43%

Example 28

(Carboxymethyl-{3,5-dichloro-4-[3-(4-chloro-benzoyl)-4-hydroxy-phenoxy]-phenyl}-amino)-acetic acid ¹H NMR: (DMSO-D6, 300 MHz): 4.12 (4H, s), 6.66-6.70 (3H, m), 6.90 (2H, s), 7.57 (2H, d, J=8.55 Hz), 7.68 (2H, d, J=8.58 Hz)
% Yield: 81%

Example 29

(Carboxymethyl-{3,5-dichloro-4-[4-hydroxy-3-(piperidine-1-carbonyl)-phenoxy]-phenyl}-amino)-acetic acid ¹H NMR: (DMSO-D6, 300 MHz): 1.43 (4H, bs), 1.54 (2H, bs), 3.15 (4H, m), 3.97 (4H, s), 6.40 (1H, m), 6.47 (2H, s), 6.67 (1H, m), 6.78 (1H, d, J=8.82 Hz)
% Yield: 32%

Example 30

({4-[3-(Bicyclo[2.2.1]hept-2-ylsulfamoyl)-4-hydroxy-phenoxy]-3,5-dichloro-phenyl}-carboxymethyl-amino)-acetic acid ¹H NMR: (DMSO-D6, 300 MHz): 1.22-1.28 (6H, m), 1.42-1.45 (2H, m), 2.07 (2H, m), 3.49 (1H, s), 3.98 (4H, s), 6.48 (2H, m), 6.91 (3H, m)
% Yield: 26%

Example 31

{Carboxymethyl-[3,5-dichloro-4-(4-hydroxy-3-isopropyl-phenoxy)-phenyl]-amino}-acetic acid $^1$H NMR: (DMSO-D6, 300 MHz): 1.10 (6H, d, J=8.8 Hz), 3.08-3.17 (1H, m), 4.14 (4H, s), 6.19-6.23 (1H, dd, J=3 Hz & 8.7 Hz), 6.62-6.67 (4H, m)
% Yield: 41%

Example 32

[[3,5-Dichloro-4-(4-hydroxy-3-isopropyl-phenoxy)-phenyl]-(4-hydroxy-phenoxycarbonyl)-amino]-acetic acid $^1$H NMR: (CDCl$_3$, 300 MHz): 1.22-1.28 (6H, m), 3.14-3.19 (1H, m), 4.46 (2H, s), 6.35-6.38 (1H, m), 6.59-6.62 (1H, m), 6.76-6.79 (2H, m), 6.87 (1H, m), 6.98 (2H, d, J=8.7 Hz), 7.49 (2H, s)
% Yield: 16%

Example 33

(Carboxymethyl-{3,5-dichloro-4-[4-hydroxy-3-(piperidine-1-sulfonyl)-phenoxy]-phenyl}-amino)-acetic acid $^1$H NMR: (CDCl$_3$, 300 MHz): 1.25 (2H, m), 1.62 (4H, m), 3.01 (4H, m), 4.23 (4H, s), 6.60 (2H, s), 6.83 (1H, m), 7.00 (1H, m), 7.05 (1H, m)
% Yield: 10%

Example 34

{[4-(3-tert-Butyl-4-hydroxy-phenoxy)-3,5-dichloro-phenyl]-carboxymethyl-amino}-acetic acid $^1$H NMR: (DMSO-D6, 300 MHz): 1.29 (9H, s), 4.14 (4H, s), 6.20-6.24 (1H, dd, J=2.87 Hz & 8.65 Hz), 6.63 (1H, d, J=8.73 Hz), 6.67 (2H, s), 6.73 (1H, d, J=2.87 Hz)
% Yield: 12%

Example 35

[[4-(3-tert-Butyl-4-hydroxy-phenoxy)-3,5-dichloro-phenyl]-(4-hydroxy-phenoxycarbonyl)-amino]-acetic acid $^1$H NMR: (CDCl$_3$, 300 MHz): 1.38 (9H, s), 4.45 (2H, s), 6.30-6.32 (1H, m), 6.49-6.52 (1H, m), 6.71-6.77 (2H, m), 6.95-6.99 (3H, m), 7.60 (2H, s)
% Yield: 98%

Example 36

{Carboxymethyl-[3,5-dichloro-4-(3-dimethylcarbamoyl-4-hydroxy-phenoxy)-phenyl]-amino}-acetic acid $^1$H NMR: (DMSO-D6, 300 MHz): 2.81 (6H, s), 4.00 (4H, s), 6.42 (1H, d, J=3 Hz), 6.48 (2H, s), 6.64-6.68 (1H, dd, J=3 Hz & 8.7 Hz), 6.79 (1H, d, J=9 Hz)
% Yield: 82%

Example 37

{Carboxymethyl-[4-(4-hydroxy-3-isopropyl-phenoxy)-3,5-dimethyl-phenyl]-amino}-acetic acid $^1$H NMR: (DMSO-D6, 400 MHz): 0.93 (6H, d, J=6.8 Hz), 1.90 (6H, s), 3.09-3.14 (1H, m), 4.02 (4H, s), 6.12-6.15 (1H, dd, J=2.8 & 8.4 Hz), 6.24 (2H, s), 6.58-6.63 (2H, m)
% Yield: 50%

Example 38

[[3,5-Dichloro-4-(3-dimethylsulfamoyl-4-hydroxy-phenoxy)-phenyl]-(4-hydroxy-phenoxycarbonyl)-amino]-acetic acid $^1$H NMR: (CDCl$_3$, 400 MHz): 2.71 (6H, s), 4.45 (2H, s), 6.76 (2H, d, J=8 Hz), 6.94 (3H, d, J=7.2 Hz), 7.02 (1H, d, J=8.8 Hz), 7.08 (1H, d, J=8 Hz), 7.51 (2H, s)
% Yield: 71%

Example 39

[[3,5-Dichloro-4-(3-dimethylcarbamoyl-4-hydroxy-phenoxy)-phenyl]-(4-hydroxy-phenoxycarbonyl)-amino]-acetic acid $^1$H NMR: (DMSO-D6, 400 MHz): 2.87 (6H, bs), 4.5 (2H, s), 6.49 (1H, d, J=2.4 Hz), 6.73 (3H, d, J=8.4 Hz), 6.82 (1H, d, J=9.2 Hz), 6.92 (2H, d, J=8.8 Hz), 7.8 (2H, s)
% Yield: 56%

Example 40

[{3,5-Dichloro-4-[4-hydroxy-3-(piperidine-1-carbonyl)-phenoxy]-phenyl}-(4-hydroxy-phenoxycarbonyl)-amino]-acetic acid $^1$H NMR: (DMSO-D6, 400 MHz): 1.41-1.52 (6H, m), 3.16-3.19 (4H, m), 4.45 (2H, s), 6.47 (1H, d, J=2.8 Hz), 6.72-6.76 (3H, m), 6.81 (1H, d, J=8.8 Hz), 6.93 (2H, d, J=8.8 Hz), 7.84 (2H, s)
% Yield: 23%

Example 41

[{3,5-Dichloro-4-[4-hydroxy-3-(piperidine-1-sulfonyl)-phenoxy]-phenyl}-(4-hydroxy-phenoxycarbonyl)-amino]-acetic acid $^1$H NMR: (CDCl$_3$, 400 MHz): 1.44 (2H, m), 1.59 (4H, m), 3.02 (4H, m), 4.46 (2H, s), 6.77 (2H, s), 6.92-7.00 (4H, m), 7.05 (1H, m), 7.51 (2H, s)
% Yield: 77%

Example 42

[[4-(4-Hydroxy-3-isopropyl-phenoxy)-3,5-dimethyl-phenyl]-(4-hydroxy-phenoxycarbonyl)-amino]-acetic acid $^1$H NMR: (DMSO-D6, 400 MHz): 1.09 (6H, d, J=6.8 Hz), 2.03 (6H, s), 3.09-3.16 (1H, m), 4.26 (2H, bs), 6.15-6.18 (1H, dd, J=2.8 Hz & 8.8 Hz), 6.62 (1H, d, J=8.8 Hz), 6.66 (1H, d, J=3.2 Hz), 6.71 (2H, d, J=8.4 Hz), 6.88 (2H, d, J=8.4 Hz), 7.19 (2H, s)
% Yield: 14%

Example 43

[{4-[3-(4-tert-Butyl-benzoyl)-4-hydroxy-phenoxy]-3,5-dichloro-phenyl}-(4-hydroxy-phenoxycarbonyl)-amino]-acetic acid $^1$H NMR: (CDCl$_3$, 400 MHz): 1.33 (9H, s), 4.39 (2H, s), 6.69-6.72 (2H, m), 6.92 (2H, d, J=8.4 Hz), 6.98 (2H, d, J=8.8 Hz), 7.26-7.32 (1H, m), 7.47-7.50 (4H, m), 7.65 (2H, d, J=6.4Hz)
% Yield: 66%

Example 44

[{3,5-Dichloro-4-[3-(4-chloro-benzoyl)-4-hydroxy-phenoxy]-phenyl}-(4-hydroxy-phenoxycarbonyl)-amino]-acetic acid $^1$H NMR: (CDCl$_3$, 400 MHz): 4.51 (2H, s), 6.79 (2H, d, J=8.4 Hz), 6.99-7.04 (4H, m), 7.07 (1H, d, J=2.8 Hz), 7.43 (2H, d, J=7.6 Hz), 7.49 (2H, s), 7.61 (2H, d, J=8 Hz)
% Yield: 68%

Example 45

[[3,5-Dichloro-4-(4-hydroxy-3-isopropylsulfamoyl-phenoxy)-phenyl]-(4-hydroxy-phenoxycarbonyl)-amino]-acetic acid $^1$H NMR: (DMSO-D6, 400 MHz): 0.93 (6H, d, J=6.8 Hz), 3.20-3.25 (1H, m), 4.24 (2H, d, J=6.4 Hz), 6.53 (2H, m), 6.65 (1H, m), 6.75 (2H, d, J=8.8 Hz), 6.84 (2H, m), 6.90-6.98 (2H, m)
% Yield 42%

Example 46

{Carboxymethyl-[3,5-dichloro-4-(3-ethyl-4-hydroxy-phenoxy)-phenyl]-amino}-acetic acid $^1$H NMR: (DMSO-D6, 400 MHz): 1.06 (3H, t, J=7.4 Hz), 2.43-2.48 (2H, m), 4.10 (4H, s), 6.28-6.31 (1H, dd, J=3.2 Hz & 8.8 Hz), 6.57 (1H, d, J=3.2 Hz), 6.63-6.66 (3H, m)
% Yield: 55%

Example 47

[{3,5-Dichloro-4-[3-(3-chloro-benzoyl)-4-hydroxy-phenoxy]-phenyl}-(4-hydroxy-phenoxycarbonyl)-amino]-acetic acid $^1$H NMR: (CDCl$_3$, 400 MHz): 4.36 (2H, bs), 6.71 (2H, d, J=6.8 Hz), 6.89 (4H, m), 6.99-7.04 (1H, m), 7.15 (1H, m), 7.47-7.51 (4H, m), 7.58 (1H, m)
% Yield: 68%

Example 48

[[3,5-Dichloro-4-(3-ethyl-4-hydroxy-phenoxy)-phenyl]-(4-hydroxy-phenoxycarbonyl)-amino]-acetic acid $^1$H NMR: (DMSO-D6, 400 MHz): 1.07 (3H, t, J=7.4 Hz), 2.44-2.48 (2H, m), 4.44 (2H, s), 6.33-6.36 (1H, dd, J=2.8 Hz & 8.4 Hz), 6.64-6.68 (2H, m), 6.73 (2H, d, J=8.8 Hz), 6.92 (2H, d, J=8.8 Hz), 7.67 (2H, s)
% Yield: 16%

Example 49

[[3,5-Dichloro-4-(6-hydroxy-biphenyl-3-yloxy)-phenyl]-(4-hydroxy-phenoxycarbonyl)-amino]-acetic acid $^1$H NMR: (CD$_3$OD, 400 MHz): 4.24 (2H, s), 6.61-6.64 (1H, m), 6.71-6.82 (4H, m), 6.96 (2H, d, J=8 Hz), 7.27 (1H, d, J=7.2 Hz), 7.35 (2H, d, J=7.2 Hz), 7.48 (2H, d, J=7.2 Hz), 7.64 (2H, s)
% Yield: 35%

Example 50

[[4-(3-Benzyl-4-hydroxy-phenoxy)-3,5-dichloro-phenyl]-(4-hydroxy-phenoxycarbonyl)-amino]-acetic acid $^1$H NMR: (CD$_3$OD, 400 MHz): 3.86 (2H, s), 4.5 (2H, s), 6.46-6.49 (2H, dd, J=2.8 Hz & 8.8 Hz), 6.69 (1H, d, J=8.4 Hz), 6.76 (2H, d, J=8.8 Hz), 6.95 (2H, d, J=7.6 Hz), 7.15-7.17 (5H, m), 7.57 (2H, s)
% Yield: 18%

Example 51

[[3,5-Dichloro-4-(3-cyclobutylsulfamoyl-4-hydroxy-phenoxy)-phenyl]-(4-hydroxy-phenoxycarbonyl)-amino]-acetic acid $^1$H NMR: (CD$_3$OD, 400 MHz): 1.47-1.59 (2H, m), 1.79-1.86 (2H, m), 1.95-1.97 (2H, m), 3.63-3.69 (1H, m), 4.45 (2H, s), 6.77 (2H, d, J=8.8Hz), 6.92-6.96 (3H, m), 7.01 (1H, d, J=3.2 Hz), 7.04 (1H, d, J=3.2 Hz), 7.68 (2H, s)
% Yield: 39%

Example 52

[{4-[3-(Bicyclo[2.2.1]hept-2-ylsulfamoyl)-4-hydroxy-phenoxy]-3,5-dichloro-phenyl}-(4-hydroxy-phenoxycarbonyl)-amino]-acetic acid $^1$H NMR: (CD$_3$OD, 400 MHz): 0.95-0.99 (2H, m), 1.06 (1H, m), 1.29-1.34 (2H, m), 1.37-1.42 (2H, m), 2.00 (2H, m), 2.14 (1H, m), 3.01-3.02 (1H, m), 4.41 (2H, s), 6.76 (2H, d, J=8.8 Hz), 6.94-6.98 (3H, m), 7.07 (2H, d, J=6.8 Hz), 7.69 (2H, s)
% Yield: 16%

Example 53

[{4-[3-(Bicyclo[2.2.1]hept-2-ylsulfamoyl)-4-hydroxy-phenoxy]-3,5-dibromo-phenyl}-(4-hydroxy-phenoxycarbonyl)-amino]-acetic acid $^1$H NMR: (DMSO-D6, 400 MHz): 0.85-0.93 (3H, m), 1.22-1.28 (3H, m), 1.35-1.45 (2H, m), 1.89 (1H, m), 2.06 (1H, m), 2.92-2.93 (1H, m), 4.23 (2H, s), 6.53 (1H, s), 6.62 (1H, d, J=5.6 Hz), 6.75 (2H, d, J=8.8 Hz), 6.83-6.93 (3H, m), 6.99 (2H, d, J=2.4 Hz),
% Yield: 14%

Example 54

[{3,5-Dichloro-4-[4-hydroxy-3-(4-hydroxy-benzoyl)-phenoxy]-phenyl}-(4-hydroxy-phenoxycarbonyl)-amino]-acetic acid $^1$H NMR: (CD$_3$OD, 400 MHz): 4.34 (2H, s), 6.76 (2H, d, J=8.8 Hz), 6.79-6.85 (3H, m), 6.98 (3H, d, J=8.8 Hz), 7.11-7.14 (1H, dd, J=3.2 Hz & 9.2 Hz), 7.56-7.58 (2H, m), 7.65 (2H, s)
% Yield: 34%

Example 55

[{3,5-Dichloro-4-[3-(4-fluoro-benzoyl)-4-hydroxy-phenoxy]-phenyl}-(4-hydroxy-phenoxycarbonyl)-amino]-acetic acid $^1$H NMR: (DMSO-D6, 400 MHz): 4.35 (2H, s), 6.53 (1H, m), 6.71-6.76 (3H, m), 6.89-6.94 (4H, m), 7.30-7.34 (2H, m), 7.74-7.77 (3H, m)
% Yield: 48%

Example 56

[(3,5-Dichloro-4-{3-[(4-chloro-phenyl)-hydroxy-methyl]-4-hydroxy-phenoxy}-phenyl)-(4-hydroxy-phenoxycarbonyl)-amino]-acetic acid $^1$H NMR: (CD$_3$OD, 400 MHz): 4.4 (2H, s), 6.01 (1H, s), 6.55-6.58 (1H, dd, J=2.8 Hz & 8.8 Hz), 6.68 (1H, d, J=8.8 Hz), 6.76 (2H, d, J=8.8 Hz), 6.85 (1H, m), 6.96 (2H, d, J=8 Hz), 7.25-7.31 (4H, m), 7.61 (2H, s)
% Yield: 90%

Example 57

[{4-[3-(Azepane-1-sulfonyl)-4-hydroxy-phenoxy]-3,5-dichloro-phenyl}-(4-hydroxy-phenoxycarbonyl)-amino]-acetic acid $^1$H NMR: (CDCl$_3$, 400 MHz): 1.52 (4H, bs), 1.64 (4H, bs), 3.27 (4H, bs), 4.46 (2H, s), 6.76 (2H, d, J=8.4 Hz), 6.96-7.02 (5H, m), 7.51 (2H, s)
% Yield: 95%

Example 58

({3,5-Dichloro-4-[3-(1-ethyl-propoxy)-4-hydroxy-phenoxy]-phenyl}-ethoxycarbonyl-amino)-acetic acid $^1$H NMR: (DMSO-D6, 400 MHz): 0.82 (6H, t, J=7.4 Hz), 1.15 (3H, t, J=7 Hz), 1.55-1.6 (4H, m), 4.06 (1H, t, J=5 Hz), 4.08-4.12 (2H, m), 4.29 (2H, s), 6.04-6.07 (1H, dd, J=2 Hz & 8.8 Hz), 6.47 (1H, m), 6.67 (1H, d, J=8.4 Hz), 7.55 (2H, s)
% Yield: 89%

Example 59

[[4-(3-sec-Butyl-4-hydroxy-phenoxy)-3,5-dimethyl-phenyl]-(4-hydroxy-phenoxycarbonyl)-amino]-acetic acid $^1$H NMR: (DMSO-D6, 400 MHz): 0.7 (3H, t, J=7.2 Hz), 1.23 (3H, d, J=7.2 Hz), 1.38-1.51 (2H, m), 2.07 (6H, s), 2.86-3.0 (1H, m), 4.27 (2H, s), 6.20-6.22 (1H, dd, J=2.4 Hz & 8.4 Hz), 6.57 (1H, d, J=2.8 Hz), 6.63 (1H, d, J=8.8 Hz), 6.71 (2H, d, J=7.6 Hz), 6.88 (2H, d, J=8.8 Hz), 7.17-7.20 (2H, m)
% Yield: 24%

Example 60

[[3,5-Dichloro-4-(3-cyclohexylsulfamoyl-4-hydroxy-phenoxy)-phenyl]-(4-hydroxy-phenoxycarbonyl)-amino]-acetic acid $^1$H NMR: (DMSO-D6, 400 MHz): 0.94-1.16 (6H, m), 1.54 (4H, d, J=8.8 Hz), 2.89 (1H, m), 4.48 (2H, s), 6.73 (2H, d, J=8.8 Hz), 6.92-6.98 (4H, m), 7.19 (1H, d, J=7.2 Hz), 7.72 (2H, s)
% Yield: 99%

Example 61

[{3,5-Dichloro-4-[4-hydroxy-3-(morpholine-4-sulfonyl)-phenoxy]-phenyl}-(4-hydroxy-phenoxycarbonyl)-amino]-acetic acid $^1$H NMR: (DMSO-D6, 400 MHz): 3.04 (4H, bs), 3.55 (4H, bs), 4.44 (2H, s), 6.73 (2H, d, J-8.4 Hz), 6.92 (2H, d, J=8.4 Hz), 7.01-7.08 (3H, m), 7.72 (2H, s)
% Yield: 10%

Example 62

({3,5-Dichloro-4-[4-hydroxy-3-(3-methyl-benzoyl)-phenoxy]-phenyl}-ethoxycarbonyl-amino)-acetic acid $^1$H NMR: (CDCl$_3$, 400 MHz): 1.36 (3H, m), 2.40 (3H, s), 4.19 (2H, m), 4.29 (2H, s), 6.99-7.09 (3H, m), 7.28-7.35 (4H, m), 7.44-7.51 (2H, m)
% Yield: 83%

Example 63

[{3,5-Dichloro-4-[4-hydroxy-3-(pyrrolidine-1-sulfonyl)-phenoxy]-phenyl}-(4-hydroxy-phenoxycarbonyl)-amino]-acetic acid $^1$H NMR: (DMSO-D6, 400 MHz): 1.71 (4H, t, J=6.4 Hz), 3.22 (4H, t, J=6.0 Hz), 4.46 (2H, s), 6.73 (2H, d, J=8.4 Hz), 6.93 (2H, d, J=8.4 Hz), 6.99-7.07 (3H, m), 7.72 (2H, s)
% Yield: 52%

Example 64

{[3,5-Dichloro-4-(4-hydroxy-3-isobutoxy-phenoxy)-phenyl]-ethoxycarbonyl-amino}-acetic acid $^1$H NMR: (CDCl$_3$, 400 MHz): 1.04 (6H, d, J=6.8 Hz), 1.25 (3H, t, J-6.6 Hz), 2.08-2.17 (1H, m), 3.79 (2H, d, J=6.8 Hz), 4.19-4.25 (2H, q, J=6.8 Hz & 6.8 Hz), 4.36 (2H, s), 6.09-6.12 (1H, dd, J==2.8 Hz & 8.8 Hz), 6.61 (1H, d, J=2.8 Hz), 6.76 (1H, d, J=8.8 Hz), 7.38 (2H, s)
% Yield: 80%

Example 65

{[3,5-Dichloro-4-(3-cyclohexylmethoxy-4-hydroxy-phenoxy)-phenyl]-ethoxycarbonyl-amino}-acetic acid $^1$H NMR: (CDCl$_3$, 400 MHz): 1.05 (3H, m), 1.26-1.32 (6H, m), 1.6-1.86 (5H, m), 3.81 (2H, d, J=6 Hz), 4.21-4.26

(2H, q, J=6.8 Hz & 7.2 Hz), 4.38 (2H, s), 6.09-6.12 (1H, dd, J=2.4 Hz & 8.8 Hz), 6.6 (1H, d, J=2.4Hz), 6.76 (1H, d, J=8.4 Hz), 7.38 (2H, s)
% Yield: 53%

Example 66

[{3,5-Dichloro-4-[4-hydroxy-3-(3-methyl-benzoyl)-phenoxy]-phenyl}-(4-hydroxy-phenoxycarbonyl)-amino]-acetic acid $^1$H NMR: (DMSO-D6, 400 MHz): 2.32 (3H, s), 4.21 (2H, bs), 6.53 (2H, m), 6.62 (2H, m), 6.75 (2H, d, J=8.8 Hz), 6.82 (1H, m), 6.89 (2H, d, J=8.8 Hz), 7.36-7.46 (4H, m)
% Yield: 32%

Example 67

[{3,5-Dibromo-4-[3-(4-chloro-benzoyl)-4-hydroxy-phenoxy]-phenyl}-(4-hydroxy-phenoxycarbonyl)-amino]-acetic acid $^1$H NMR: (DMSO-D6, 400 MHz): 4.43 (2H, s), 6.73 (3H, d, J=8.8 Hz), 6.90-6.95 (4H, m), 7.57 (2H, d, J=8.4 Hz), 7.68 (2H, d, J=8.4 Hz), 7.83 (2H, s)
% Yield: 42%

Example 68

({3,5-Dibromo-4-[3-(4-chloro-benzoyl)-4-hydroxy-phenoxy]-phenyl}ethoxycarbonyl-amino)-acetic acid $^1$H NMR: (DMSO-D6, 400 MHz): 1.14 (3H, t, J=6.8 Hz), 4.05-4.11 (2H, q, J=6.8 Hz & 6.8 Hz), 4.22 (2H, s), 6.71 (1H, d, J=2.4 Hz), 6.92-6.96 (2H, m), 7.57 (2H, d, J=8.4 Hz), 7.68-7.71 (4H, m)
% Yield: 98%

Example 69

({3,5-Dichloro-4-[4-hydroxy-3-(4-methyl-benzoyl)-phenoxy]-phenyl}-ethoxycarbonyl-amino)-acetic acid $^1$H NMR: (DMSO-D6, 400 MHz): 1.14 (3H, t, J=7 Hz), 2.36 (3H, s), 4.06-4.12 (2H, q, J=6.8 Hz & 6.8 Hz), 4.32 (2H, s), 6.68 (1H, d, J=2.4Hz), 6.92-6.98 (2H, m), 7.30 (2H, d, J=8 Hz), 7.55-7.59 (4H, m)
% Yield: 95%

Example 70

[{3,5-Dichloro-4-[4-hydroxy-3-(4-methyl-benzoyl)-phenoxy]-phenyl}-(4-hydroxy-phenoxycarbonyl)-amino]-acetic acid $^1$H NMR: (DMSO-D6, 400 MHz): 2.34 (3H, s), 4.22 (2H, s), 6.53 (1H, s), 6.60-6.65 (2H, m), 6.71-6.76 (1H, m), 6.82-6.85 (1H, m), 6.89-6.96 (3H, m), 7.31 (2H, d, J=4.8 Hz), 7.57 (2H, d, J=8.0 Hz), 7.83 (1H, s)
% Yield: 55%

Example 71

{[3,5-Dichloro-4-(3-isopropyl-4-methoxy-phenoxy)-phenyl]-ethoxycarbonyl-amino}-acetic acid ethyl ester $^1$H NMR: (CDCl$_3$, 300 MHz): 1.19 (6H, d, J=6.4 Hz), 1.29-1.35 (6H, m), 3.24-3.31 (1H, m), 3.76 (3H, s), 4.19-4.28 (4H, m), 4.31 (2H, s), 6.43-6.46 (1H, dd, J=2.8 Hz & 8.8 Hz), 6.69 (1H, d, J=8.8 Hz), 6.87 (1H, d, J=2.8 Hz), 7.38 (2H, s)

Example 72

{[4-(4-Benzyloxy-3-isopropyl-phenoxy)-3,5-dichloro-phenyl]-ethoxycarbonyl-amino}-acetic acid ethyl ester $^1$H NMR: (CDCl$_3$, 300 MHz): 1.24 (6H, d, J=6.9 Hz), 1.31 (6H, t, J=7.2 Hz), 3.35-3.40 (1H, m), 4.21-4.24 (4H, m), 4.31 (2H, s), 5.01 (2H, s), 6.41-6.45 (1H, dd, J=2.9 Hz & 8.7 Hz), 6.77 (1H, d, J=8.9 Hz), 6.90 (1H, d, J=2.4 Hz), 7.34-7.44 (7H, m)

Example 73

{[4-(3-sec-Butyl-4-methoxy-phenoxy)-3,5-dichloro-phenyl]-ethoxycarbonyl-amino}-acetic acid ethyl ester $^1$H NMR: (CDCl$_3$, 300 MHz): 0.83 (3H, t, J=7.35 Hz), 1.16 (3H, d, J=6.93 Hz), 1.23-1.26 (2H, m), 1.28-1.33 (4H, m), 1.33-1.53 (2H, m), 3.03-3.10 (1H, m), 3.77 (3H, s), 4.18-4.27 (4H, m), 4.31 (2H, s), 6.45-6.49 (1H, dd, J=3.0 Hz & 8.79 Hz), 6.74 (1H, d, J=8.6 Hz), 6.8 (1H, d, J=2.91 Hz), 7.47 (2H, s)

Example 74

{[4-(3-Benzyl-4-methoxy-phenoxy)-3,5-dichloro-phenyl]-ethoxycarbonyl-amino}-acetic acid ethyl ester $^1$H NMR: (CDCl$_3$, 300 MHz): 1.25-1.38 (6H, m), 3.7 (3H, s), 3.93 (2H, s), 4.12-4.30 (6H, m), 6.54-6.57 (1H, dd, J=3.09 Hz & 8.7 Hz), 6.69-6.75 (2H, m), 7.17-7.36 (5H, m), 7.45 (2H, s)

Example 75

({4-[3-(Bicyclo[2.2.1]hept-2-ylcarbamoyl)-4-methoxy-phenoxy]-3,5-dichloro-phenyl}-ethoxycarbonyl-amino)-acetic acid ethyl ester $^1$H NMR: (CDCl$_3$, 300 MHz): 1.13-1.19 (2H, m), 1.26-1.31 (7H, m), 1.50 (2H, m), 1.54 (3H, m), 1.82-1.88 (1H, m), 2.30 (2H, s), 3.93 (3H, s), 4.18-4.27 (4H, q, J=7.02 Hz & 7.14 Hz), 4.30 (2H, s), 6.93 (1H, d, J=8.88 Hz), 7.02 (1H, m), 7.37 (2H, s), 7.61 (1H, d, J=2.6 Hz)

Example 76

{[3,5-Dichloro-4-(3-ethyl-4-methoxy-phenoxy)-phenyl]-ethoxycarbonyl-amino}-acetic acid ethyl ester $^1$H NMR: (CDCl$_3$, 300 MHz): 1.17 (3H, t, J=7.5 Hz), 1.24-1.26 (3H, m), 1.28-1.33 (3H, m) 2.56-2.64 (2H, q, J=7.44 Hz & 7.47 Hz), 3.78 (3H, s), 4.22-4.29 (4H, m), 4.31

(2H, s) 6.50-6.54 (1H, dd, J=3.03 Hz & 8.79 Hz), 6.71 (1H, d, J=8.8 Hz), 6.77 (1H, d, J=3 Hz), 7.39 (2H, s)

Example 77

{[3,5-Dichloro-4-(3-dimethylcarbamoyl-4-methoxy-phenoxy)-phenyl]-ethoxycarbonyl-amino}-acetic acid ethyl ester $^1$H NMR: (CDCl$_3$, 300 MHz): 1.24-1.33 (6H, m), 2.84 (3H, s), 3.08 (3H, s), 3.79 (3H, s), 4.19-4.29 (4H, m), 4.31 (2H, s), 6.70 (1H, d, J=2.7 Hz), 6.81-6.90 (2H, m), 7.38 (2H, s)

Example 78

{[3,5-Dichloro-4-(3-cyclobutylcarbamoyl-4-methoxy-phenoxy)-phenyl]-ethoxycarbonyl-amino}-acetic acid ethyl ester $^1$H NMR: (CDCl$_3$, 300 MHz): 1.23-1.34 (6H, m), 1.77-1.80 (2H, m), 1.91-1.97 (2H, m), 2.41 (2H, bs), 3.95 (3H, s), 4.20-4.27 (4H, q, J=6.93 Hz & 7.08 Hz), 4.30 (2H, s), 4.47-4.55 (1H, m), 6.94 (1H, d, J=8.9 Hz), 7.03 (1H, m), 7.37 (2H, s), 7.60 (1H, s)

Example 79

{[3,5-Dichloro-4-(4-methoxy-3-propyl-phenoxy)-phenyl]-ethoxycarbonyl-amino}-acetic acid ethyl ester $^1$H NMR: (DMSO-D6, 300 MHz): 0.85 (3H, t, J=7.32 Hz), 1.13-1.22 (6H, m), 1.44-1.52 (2H, m), 2.44-2.48 (2H, m), 3.71 (3H, s), 4.07-4.19 (4H, m), 4.43 (2H, s), 6.48-6.52 (1H, dd, J=3.09 Hz & 8.85 Hz), 6.68 (1H, d, J=3 Hz), 6.86 (1H, d, J=8.9Hz), 7.56 (2H, s)

Example 80

{[3,5-Dichloro-4-(3-isopropylcarbamoyl-4-methoxy-phenoxy)-phenyl]-ethoxycarbonyl-amino}-acetic acid ethyl ester $^1$H NMR: (CDCl$_3$, 300 MHz): 1.22-1.34 (12H, m), 3.95 (3H, s), 4.20-4.27 (5H, m), 4.31 (2H, s), 6.92 (1H, d, J=9 Hz), 7.38 (2H, m), 7.62 (1H, m), 7.78 (1H, d, J=6.9 Hz)

Example 81

{[3,5-Dichloro-4-(6-methoxy-biphenyl-3-yloxy)-phenyl]-ethoxycarbonyl-amino}-acetic acid ethyl ester $^1$H NMR: (CDCl$_3$, 300 MHz): 1.23-1.33 (6H, m), 3.76 (3H, s), 4.20-4.28 (4H, m), 4.30 (2H, s), 6.80 (1H, d, J=3 Hz), 6.85 (1H, d, J=2.7 Hz), 6.91 (1H, m), 7.26 (1H, m), 7.29-7.41 (4H, m), 7.50 (2H, d, J=7 Hz)

Example 82

({3,5-Dichloro-4-[3-(4-fluoro-benzoyl)-4-methoxy-phenoxy]-phenyl}-ethoxycarbonyl-amino)-acetic acidethyl ester $^1$H NMR: (CDCl$_3$, 300 MHz): 1.23-1.30 (6H, m), 3.69 (3H, s), 4.20-4.28 (4H, m), 4.30 (2H, s), 6.85 (1H, d, J=3 Hz), 6.90-7.0 (2H, m), 7.07-7.13 (2H, m), 7.38 (2H, s), 7.81-7.86 (2H, m)

Example 83

{[3,5-Dichloro-4-(3-diethylcarbamoyl-4-methoxy-phenoxy)-phenyl]-ethoxycarbonyl-amino}-acetic acid ethyl ester $^1$H NMR: (DMSO-D6, 300 MHz): 0.91 (3H, t, J=6.9 Hz), 1.07 (3H, t, J=7.0 Hz), 1.12-1.22 (6H, m), 3.01-3.03 (4H, m), 3.72 (3H, s), 4.02-4.18 (4H, m), 4.43 (2H, s), 6.51 (1H, d, J=3 Hz), 6.84-6.88 (1H, dd, J=3 Hz & 9 Hz), 7.04 (1H, d, J=9Hz), 7.58 (2H, s)

Example 84

({3,5-Dichloro-4-[3-(5-chloro-thiophene-2-carbonyl)-4-methoxy-phenoxy]-phenyl}-ethoxycarbonyl-amino)-acetic acid ethyl ester $^1$H NMR: (CDCl$_3$, 300 MHz): 1.23-1.321 (6H, m), 3.77 (3H, s), 4.22-4.28 (4H, m), 4.30 (2H, s), 6.84 (2H, s), 6.92-6.97 (3H, m), 7.38 (2H, s)

Example 85

{[4-(3-sec-Butyl-4-methoxy-phenoxy)-3,5-dimethyl-phenyl]-ethoxycarbonyl-amino}-acetic acid ethyl ester $^1$H NMR: (CDCl$_3$, 300 MHz): 0.83 (6H, t, J=6.2 Hz), 1.03-1.32 (6H, m), 1.49-1.60 (2H, m), 2.10 (6H, s), 3.11-3.18 (1H, m), 4.20-4.27 (4H, m), 4.31 (2H, s), 4.99 (2H, s), 6.37 (1H, d, J=6 Hz), 6.74 (2H, d, J=8.7 Hz), 7.02 (2H, s), 7.31-7.43 (5H, m)

Example 86

{[3,5-Dichloro-4-(4-methoxy-3-phenylcarbamoyl-phenoxy)-phenyl]-ethoxycarbonyl-amino}-acetic acid ethyl ester $^1$H NMR: (CDCl$_3$, 300 MHz): 1.26-1.29 (6H, m), 4.04 (3H, s), 4.19-4.28 (4H, m), 4.32 (2H, s) 7.01 (1H, d, J=9 Hz), 7.09-7.14 (2H, m), 7.32-7.39 (4H, m), 7.62-7.70 (3H, m)

Example 87

({3,5-Dichloro-4-[3-(4-chloro-benzoyl)-4-methoxy-phenoxy]-phenyl}-ethoxycarbonyl-amino)-acetic acid ethyl ester $^1$H NMR: (CDCl$_3$, 300 MHz): 1.28-1.32 (6H, m), 3.68 (3H, s), 4.18-4.30 (4H, m), 4.31 (2H, s), 6.82-6.86 (1H, m), 6.92 (1H, d, J=8.8 Hz), 6.97-7.01 (1H, m), 7.38-7.42 (4H, m), 7.72-7.75 (2H, m)

Example 88

({3,5-Dichloro-4-[3-(2,4-dichloro-benzoyl)-4-methoxy-phenoxy]-phenyl}-ethoxycarbonyl-amino)-acetic acid ethyl ester $^1$H NMR: (CDCl$_3$, 300 MHz): 1.26-1.31 (6H, m), 3.58 (3H, s), 4.19-4.29 (4H, m), 4.32 (2H, s), 6.86 (1H, d, J=9 Hz), 7.05-7.15 (2H, m), 7.30-7.40 (3H, m), 7.51 (2H, s)

Example 89

[[4-(3-sec-Butyl-4-methoxy-phenoxy)-3,5-dichlorophenyl]-(4-methoxy-phenoxycarbonyl)-amino]-acetic acid ethyl ester $^1$H NMR: (CDCl$_3$, 300 MHz): 0.83 (3H, t, J=7.5 Hz), 1.16 (3H, d, J=7.2 Hz), 1.23-1.34 (3H, m), 1.48-1.62 (2H, m), 3.02-3.09 (1H, m), 3.76 (3H, s), 3.79 (3H, s), 4.27-4.29 (2H, m), 4.39 (2H, bs), 6.44-6.48 (1H, dd, J=3 Hz & 8.7 Hz), 6.70 (1H, d, J=8.7 Hz), 6.82 (1H, d, J=3 Hz), 6.88 (2H, d, J=8.7 Hz), 7.05 (2H, d, J=8.7 Hz), 7.49 (2H, s)

Example 90

({4-[3-(4-tert-Butyl-benzoyl)-4-methoxy-phenoxy]-3,5-dichloro-phenyl}-ethoxycarbonyl-amino)-acetic acid ethyl ester $^1$H NMR: (CDCl$_3$, 300 MHz): 1.28-1.32 (6H, m), 1.35 (9H, s), 3.7 (3H, s), 4.15-4.28 (4H, m), 4.29 (2H, s), 6.82 (1H, m), 6.91-6.94 (2H, m), 7.37 (2H, m), 7.43-7.50 (2H, m), 7.75-7.78 (2H, m)

Example 91

{[4-(3-sec-Butyl-4-methoxy-phenoxy)-3,5-dichlorophenyl]-ethoxycarbonylmethyl-amino}-acetic acid ethyl ester $^1$H NMR: (CDCl$_3$, 400 MHz): 0.83 (3H, t, J=7.4 Hz), 1.15 (3H, d, J=6.8 Hz), 1.24-1.28 (6H, m), 1.5-1.6 (2H, m), 3.04-3.05 (1H, m), 3.76 (3H, s), 4.10 (4H, s), 4.22-4.28 (4H, m), 6.44-6.47 (1H, dd, J=2.8 Hz & 8.8 Hz), 6.59 (2H, s), 6.69 (1H, d, J=9.2 Hz), 6.78 (1H, d, J=3.2 Hz)

Example 92

({3,5-Dichloro-4-[3-(4-chloro-benzoyl)-4-methoxy-phenoxy]-phenyl}-ethoxycarbonylmethyl-amino)-acetic acid ethyl ester $^1$H NMR: (CDCl$_3$, 300 MHz): 1.24-1.29 (6H, m), 3.68 (3H, s), 4.09 (4H, s), 4.14-4.31 (4H, m), 6.57 (2H, m), 6.84-6.94 (3H, m), 7.40 (2H, d, J=8.43 Hz), 7.75 (2H, d, J=8.43 Hz)

Example 93

[[3,5-Dichloro-4-(3-isopropyl-4-methoxy-phenoxy)-phenyl]-(4-methoxy-phenoxycarbonyl)-amino]-acetic acid ethyl ester $^1$H NMR: (CDCl$_3$, 300 MHz): 1.19 (6H, d, J=6.84 Hz), 1.28-1.34 (3H, m), 3.25-3.30 (1H, m), 3.77 (3H, s), 3.79 (3H, s), 4.26-4.29 (2H, m), 4.40 (2H, bs), 6.41-6.45 (1H, dd, J=3.03 Hz & 8.79 Hz), 6.69 (1H, d, J=8.88 Hz), 6.86-6.89 (3H, m), 7.05 (2H, d, J=8.79 Hz), 7.50 (2H, s)

Example 94

[[4-(3-tert-Butyl-4-methoxy-phenoxy)-3,5-dichlorophenyl]-(4-methoxy-phenoxycarbonyl)-amino]-acetic acid ethyl ester $^1$H NMR: (CDCl$_3$, 300 MHz): 1.26-1.29 (3H, m), 1.35 (9H, s), 3.78 (3H, s), 3.79 (3H, s), 4.29 (2H, m), 4.39 (2H, bs), 6.40-6.44 (1H, dd, J=3 Hz & 8.79 Hz), 6.7 (1H, d, J=8.85 Hz), 6.88 (2H, d, J=8.67 Hz), 6.99-7.06 (3H, m), 7.50 (2H, s)

Example 95

[[3,5-Dichloro-4-(3-dimethylsulfamoyl-4-methoxy-phenoxy)-phenyl]-(4-methoxy-phenoxycarbonyl)-amino]-acetic acid ethyl ester $^1$H NMR: (CDCl$_3$, 400 MHz): 1.14 (3H, t, J=11.2 Hz), 2.83 (6H, s), 3.79 (3H, s), 3.89 (3H, s), 4.29 (2H, m), 4.40 (2H, bs), 6.59-6.86 (2H, m), 6.95 (2H, d, J=9.2 Hz), 7.04 (2H, d, J=8.8 Hz), 7.41 (1H, s), 7.51 (2H, s)

Example 96

[[3,5-Dichloro-4-(3-dimethylcarbamoyl-4-methoxy-phenoxy)-phenyl]-(4-methoxy-phenoxycarbonyl)-amino]-acetic acid ethyl ester $^1$H NMR: (CDCl$_3$, 300 MHz): 1.29-1.34 (3H, m), 2.84 (3H, s), 3.08 (3H, s), 3.8 (6H, s), 4.20-4.29 (2H, m), 4.40 (2H, s), 6.71 (1H, d, J=2.64 Hz), 6.82-6.89 (4H, m), 7.05 (2H, d, J=8.8 Hz), 7.69 (2H, s)

Example 97

[{3,5-Dichloro-4-[4-methoxy-3-(piperidine-1-sulfonyl)-phenoxy]-phenyl}-(4-methoxy-phenoxycarbonyl)-amino]-acetic acid ethyl ester $^1$H NMR: (CDCl$_3$, 400 MHz): 1.30-1.34 (6H, m), 1.50-1.52 (3H, m), 3.17-3.2 (4H, m), 3.79 (3H, s), 3.88 (3H, s), 4.28-4.29 (2H, m), 4.40 (2H, bs), 6.87 (2H, d, J=8.4 Hz), 6.93 (1H, d, J=8.8Hz), 6.99-7.05 (3H, m), 7.40 (1H, d, J=3.2 Hz), 7.51 (2H, s)

Example 98

[[4-(3-Isopropyl-4-methoxy-phenoxy)-3,5-dimethylphenyl]-(4-methoxy-phenoxycarbonyl)-amino]-acetic acid ethyl ester $^1$H NMR: (CDCl$_3$, 400 MHz): 1.17 (6H, d, J=6.8 Hz), 1.27-1.32 (3H, m), 2.12 (6H, s), 3.23-3.30 (1H, m), 3.76 (6H, s), 4.24-4.27 (2H, m), 4.38 (2H, s), 6.32-6.35 (1H, dd, J=3 Hz & 8.7 Hz), 6.65 (1H, d, J=8.8 Hz), 6.80 (1H, d, J=2.8 Hz), 6.84-6.86 (2H, m), 7.03-7.05 (2H, m), 7.14 (2H, s)

Example 99

[{4-[3-(4-tert-Butyl-benzoyl)-4-methoxy-phenoxy]-3,5-dichloro-phenyl}-(4-methoxy-phenoxycarbonyl)-amino]-acetic acid ethyl ester $^1$H NMR: (CDCl$_3$, 400 MHz): 1.24-1.33 (12H, m), 3.70 (3H, s), 3.79 (3H, s), 4.27 (2H, s), 4.37 (2H, s), 6.83-6.94 (5H, m), 7.03 (2H, d, J=8.4Hz), 7.44 (2H, d, J=8.4Hz), 7.49 (2H, s), 7.76 (2H, d, J=8.4 Hz)

Example 100

[{3,5-Dichloro-4-[3-(4-chloro-benzoyl)-4-methoxy-phenoxy]-phenyl}-(4-methoxy-phenoxycarbonyl)-amino]-acetic acid ethyl ester $^1$H NMR: (CDCl$_3$, 400 MHz): 1.24 (3H, t, J=7.2 Hz), 3.66 (3H, s), 3.85 (3H, s), 4.27 (2H, m), 4.38 (2H, s), 6.86-6.9 (4H, m), 6.98-7.04 (3H, m), 7.38 (2H, d, J=2.4 Hz), 7.5 (2H, s), 7.72 (2H, d, J=6.8 Hz)

Example 101

[[3,5-Dichloro-4-(3-isopropylsulfamoyl-4-methoxy-phenoxy-phenyl]-(4-methoxy-phenoxycarbonyl)-amino]-acetic acid ethyl ester $^1$H NMR: (CDCl$_3$, 400 MHz): 1.05 (6H, d, J=6.8 Hz), 1.32 (3H, t, J=6.8 Hz), 3.4-3.45 (1H, m), 3.79 (3H, s), 3.95 (3H, s), 4.28 (2H, bs), 4.41 (2H, s), 6.87 (2H, d, J=8.8 Hz), 6.96 (1H, d, J=8.8 Hz), 7.04 (3H, d, J=8.8 Hz), 7.41 (1H, d, J=2.8 Hz), 7.52 (2H, s)

Example 102

{[3,5-Dichloro-4-(3-ethyl-4-methoxy-phenoxy)-phenyl]-ethoxycarbonylmethyl-amino}-acetic acid ethyl ester $^1$H NMR: (CDCl$_3$, 400 MHz): 1.16 (3H, t, J=7.6 Hz), 1.26-1.32 (6H, m), 2.58-2.60 (2H, m), 3.77 (3H, s), 4.11 (4H, s), 4.23-4.28 (4H, q, J=6.8 Hz & 7.2 Hz), 6.52-6.53 (1H, m), 6.60 (2H, s), 6.6 (1H, d, J=8.8 Hz), 6.74 (1h, d, J=3.4 Hz)

Example 103

[{3,5-Dichloro-4-[3-(3-chloro-benzoyl)-4-methoxy-phenoxy]-phenyl}-(4-methoxy-phenoxycarbonyl)-amino]-acetic acid ethyl ester $^1$H NMR: (CDCl$_3$, 400 MHz): 1.24-1.32 (3H, m), 3.68 (3H, s), 3.79 (3H, s), 4.27 (2H, bs), 4.37-4.45 (2H, m), 6.86-6.88 (3H, m), 6.93 (1H, d, J=8.4 Hz), 6.99-7.04 (3H, m), 7.34-7.38 (1H, m), 7.50-7.53 (3H, m), 7.64-7.66 (1H, m), 7.77 (1H, s)

Example 104

[[3,5-Dichloro-4-(3-ethyl-4-methoxy-phenoxy)-phenyl]-(4-methoxy-phenoxycarbonyl)-amino]-acetic acid ethyl ester $^1$H NMR: (CDCl$_3$, 400 MHz): 1.17 (3H, t, J=7.4 Hz), 1.3 (2H, t, J=7.2 Hz), 2.57-2.63 (2H, q, J=7.6 Hz & 7.6 Hz), 3.78 (6H, s), 4.28 (2H, m), 4.39 (2H, s), 6.50-6.53 (1H, dd, J=3.2 Hz & 8.8 Hz), 6.7 (1H, d, J=8.8 Hz), 6.77 (1H, s), 6.88 (2H, d, J=8.8 Hz), 7.05 (2H, d, J=8.8 Hz), 7.50 (2H, s)

Example 105

[[3,5-Dichloro-4-(6-methoxy-biphenyl-3-yloxy)-phenyl]-(4-methoxy-phenoxycarbonyl)-amino]-acetic acid ethyl ester $^1$H NMR: (CDCl$_3$, 400 MHz): 1.24-1.32 (3H, t, J=7.0 Hz), 3.76 (3H, s), 3.79 (3H, s), 4.27-4.38 (2H, m), 4.45 (2H, bs), 6.76-6.79 (1H, dd, J=3.2 Hz & 8.8 Hz), 6.86-6.89 (4H, m), 7.04 (2H, d, J=8.4 Hz), 7.25-7.33 (1H, m), 7.36-7.40 (2H, m), 7.49-7.51 (4H, m)

Example 106

[[4-(3-Benzyl-4-methoxy-phenoxy)-3,5-dichloro-phenyl]-(4-methoxy-phenoxycarbonyl)-amino]-acetic acid ethyl ester $^1$H NMR: (CDCl$_3$, 400 MHz): 1.24-1.33 (3H, m), 3.75 (3H, s), 3.79 (3H, s), 3.93 (2H, s), 4.28-4.39 (2H, m), 4.42 (2H, s), 6.54-6.57 (1H, dd, J=2.8 Hz & 8.8 Hz), 6.69-6.74 (2H, m), 6.87 (2H, d, J=8.8 Hz), 7.04 (2H, d, J=8.4 Hz), 7.13-7.18 (3H, m), 7.22-7.25 (2H, m), 7.47 (2H, s)

Example 107

[[3,5-Dichloro-4-(3-cyclobutylsulfamoyl-4-methoxy-phenoxy)-phenyl]-(4-methoxy-phenoxycarbonyl)-amino]-acetic acid ethyl ester $^1$H NMR: (CDCl$_3$, 400 MHz): 1.32 (3H, t, J=7.2 Hz), 1.51-1.56 (2H, m), 1.69-1.75 (2H, m), 1.98-2.03 (2H, m), 3.74 (1H, m), 3.79 (3H, s), 3.96 (3H, s), 4.29 (2H, m), 4.41 (2H, s), 6.87 (2H, d, J=8.4 Hz), 6.96 (1H, d, J=9.2 Hz), 7.04 (3H, d, J=8.81 Hz), 7.37 (1H, d, J=2.8 Hz), 7.52 (2H, s)

Example 108

[{4-[3-(Bicyclo[2.2.1]hept-2-ylsulfamoyl)-4-methoxy-phenoxy]-3,5-dichloro-phenyl}-(4-methoxy-phenoxycarbonyl)-amino]-acetic acid ethyl ester $^1$H NMR: (CDCl$_3$, 400 MHz): 0.98-1.01 (2H, m), 1.10-1.19 (2H, m), 1.26-1.27 (2H, m), 1.30-1.34 (4H, m), 1.37-1.40 (3H, m), 3.09-3.11 (1H, m), 3.79 (3H, s), 3.94 (3H, s), 4.29 (2H, m), 4.41 (2H, bs), 6.87 (2H, d, J=8.8 Hz), 6.97 (1H, d, J=9.2 Hz), 7.03-7.06 (3H, m), 7.41 (1H, s), 7.52 (2H, s)

Example 109

[{4-[3-(Bicyclo[2.2.1]hept-2-ylsulfamoyl)-4-methoxy-phenoxy]-3,5-dibromo-phenyl}-(4-methoxy-phenoxycarbonyl)-amino]-acetic acid ethyl ester $^1$H NMR: (CDCl$_3$, 400 MHz): 0.98-1.00 (2H, m), 1.10-1.19 (2H, m), 1.30-1.39 (5H, m), 2.03-2.04 (2H, m), 2.17-2.20 (2H, m), 3.09-3.14 (1H, m), 3.79 (3H, s), 3.94 (3H, s), 4.29 (2H, m), 4.48 (2H, s), 6.87 (2H, d, J-8.4 Hz), 6.96-6.99 (1H, m), 7.05 (3H, d, J=8.8 Hz), 7.39 (1H, d, J=2.8 Hz), 7.72 (2H, s)

Example 110

[{3,5-Dichloro-4-[4-methoxy-3-(4-methoxy-benzoyl)-phenoxy]-phenyl}-(4-methoxy-phenoxycarbonyl)-amino]-acetic acid ethyl ester $^1$H NMR: (CDCl$_3$, 400 MHz): 1.28-1.32 (3H, m), 3.70 (3H, s), 3.81 (3H, s), 3.86 (3H, s), 4.26 (2H, s), 4.37-4.45 (2H, m), 6.83 (1H, d, J=3.2 Hz), 6.85-6.94 (6H, m), 7.03 (2H, d, J=8.4 Hz), 7.49 (2H, s), 7.78-7.81 (2H, m)

Example 111

[{3,5-Dichloro-4-[3-(4-fluoro-benzoyl)-4-methoxy-phenoxy]-phenyl}-(4-methoxy-phenoxycarbonyl)-amino]-acetic acid ethyl ester $^1$H NMR: (CDCl$_3$, 400 MHz): 1.31 (3H, t, J=7.2 Hz), 3.68 (3H, s), 3.79 (3H, s), 4.27 (2H, bs), 4.45 (2H, bs), 6.86-6.92 (2H, m), 7.02-7.11 (3H, m), 7.49 (2H, s), 7.81-7.84 (2H, m)

Example 112

[{4-[3-(Azepane-1-sulfonyl)-4-methoxy-phenoxy]-3,5-dichloro-phenyl}-(4-methoxy-phenoxycarbonyl)-amino]-acetic acid ethyl ester $^1$H NMR: (CDCl$_3$, 400 MHz): 1.32 (3H, t, J=7.0 Hz), 1.60-1.61 (4H, m), 1.71 (4H, bs), 3.31-3.34 (4H, m), 3.79

(3H, s), 3.88 (3H, s), 4.29 (2H, m), 4.47 (2H, s), 6.86-6.92 (3H, m), 6.97-6.99 (1H, in), 7.04 (2H, d, J=8.8 Hz), 7.44 (1H, d, J=3.2 Hz), 7.51 (2H, s)

Example 113

({4-[4-Benzyloxy-3-(1-ethyl-propoxy)-phenoxy]-3,5-dichloro-phenyl}-ethoxycarbonyl-amino)-acetic acid ethyl ester $^1$H NMR: (CDCl$_3$, 400 MHz): 0.95 (6H, t, J=7.2Hz), 1.3 (6H, t, J=7.2 Hz), 1.64-1.74 (4H, m), 4.09-4.13 (1H, m), 4.19-4.28 (4H, m), 4.3 (2H, s), 5.04 (2H, s), 6.15-6.18 (1H, dd, J=2.4 Hz & 8.8 Hz), 6.57 (1H, d, J=2 Hz), 6.78 (2H, d, J=8.8 Hz), 7.30-7.43 (7H, m)

Example 114

[[4-(3-sec-Butyl-4-methoxy-phenoxy)-3,5-dimethyl-phenyl]-(4-methoxy-phenoxycarbonyl)-amino]-acetic acid ethyl ester $^1$H NMR: (CDCl$_3$, 400 MHz): 0.82 (3H, t, J=7.2 Hz), 1.14 (3H, d, J=6.8 Hz), 1.30 (3H, t, J=6.8 Hz), 1.45-1.60 (2H, m), 2.12 (6H, s), 3.01-3.06 (1H, m), 3.74 (3H, s), 3.78 (3H, s), 4.24-4.27 (2H, m), 4.38-4.48 (2H, m), 6.35-6.38 (1H, dd, J=2.8 Hz & 8.8 Hz), 6.66 (1H, d, J=8.8Hz), 6.72 (1H, d, J=2.8 Hz), 6.85 (2H, d, J=8.4 Hz), 7.04 (2H, d, J=8.8 Hz), 7.14 (2H, s)

Example 115

[[3,5-Dichloro-4-(3-cyclohexylsulfamoyl-4-methoxy-phenoxy)-phenyl]-(4-methoxy-phenoxycarbonyl)-amino]-acetic acid ethyl ester $^1$H NMR: (CDCl$_3$, 400 MHz): 1.11-1.27 (8H, m), 1.29-1.34 (3H, m), 1.68-1.72 (2H, m), 3.11-3.13 (1H, m), 3.79 (3H, s), 3.94 (3H, s), 4.25-4.28 (2H, m), 4.41 (2H, bs), 4.83 (1H, d, J=7.6 Hz), 6.87 (2H, d, J=8.0 Hz), 6.94-6.97 (1H, m), 7.05 (3H, d, J=8.4 Hz), 7.40-7.41 (1H, m), 7.52 (2H, s)

Example 116

[{3,5-Dichloro-4-[4-methoxy-3-(morpholine-4-sulfonyl)-phenoxy]-phenyl}-(4-methoxy-phenoxycarbonyl)-amino]-acetic acid ethyl ester $^1$H NMR: (CDCl$_3$, 400 MHz): 1.32 (3H, t, J=7.2 Hz), 3.23 (4H, t, J=4.8 Hz), 3.71 (4H, t, J=4.8 Hz), 3.79 (3H, s), 3.89 (3H, s), 4.41 (2H, m), 4.46 (2H, s), 6.87 (2H, d, J=8.8 Hz), 6.92 (1H, d, J=4.8 Hz), 6.95-7.03 (3H, m), 7.4 (1H, d, J=2.8 Hz), 7.52 (2H, s)

Example 117

[{3,5-Dichloro-4-[4-methoxy-3-(pyrrolidine-1-sulfonyl)-phenoxy]-phenyl}-(4-methoxy-phenoxycarbonyl)-amino]-acetic acid ethyl ester $^1$H NMR: (DMSO-D6, 400 MHz): 1.32 (3H, t, J=7.2 Hz), 1.81-1.84 (4H, m), 3.36-3.39 (4H, m), 3.79 (3H, s), 3.90 (3H, s), 4.29 (2H, m), 4.40-4.47 (2H, bs), 6.87 (2H, d, J=8.8 Hz), 6.94 (1H, d, J=8.8 Hz), 7.04 (3H, d, J=8.8 Hz), 7.44 (1H, d, J=2.8 Hz), 7.51 (2H, s)

Example 118

{[4-(4-Benzyloxy-3-isobutoxy-phenoxy)-3,5-dichloro-phenyl]-ethoxycarbonyl-amino}-acetic acid ethyl ester $^1$H NMR: (CDCl$_3$, 400 MHz): 1.05 (6H, d, J=6.8 Hz), 1.26-1.32 (6H, m), 2.12-2.19 (1H, m), 3.77 (2H, d, J=6.4 Hz), 4.19-4.28 (4H, m), 4.31 (2H, s), 5.05 (2H, s), 6.08-6.11 (1H, dd, J=2.4 Hz & 8.4 Hz), 6.64 (1H, d, J=2.8 Hz), 6.77 (1H, d, J=8.8 Hz), 7.29-7.30 (1H, m), 7.33-7.38 (4H, m), 7.42-7.44 (2H, m)

Example 119

[{3,5-Dichloro-4-[4-methoxy-3-(3-methyl-benzoyl)-phenoxy]-phenyl}-(4-methoxy-phenoxycarbonyl)-amino]-acetic acid ethyl ester $^1$H NMR: (CDCl$_3$, 400 MHz): 1.30 (3H, t, J=7.2 Hz), 2.37 (3H, s), 3.68 (3H, s), 3.78 (3H, s), 4.27 (2H, s), 4.37-4.45 (2H, bs), 6.84-6.87 (3H, m), 6.92 (1H, d, J=9.2 Hz), 7.02 (3H, d, J=8 Hz), 7.30 (1H, d, J=7.6 Hz), 7.35 (1H, d, J=7.2 Hz), 7.49 (2H, s), 7.56 (1H, d, J=7.6 Hz), 7.64 (1H, s)

Example 120

[{3,5-Dibromo-4-[3-(4-chloro-benzoyl)-4-methoxy-phenoxy]-phenyl}-(4-methoxy-phenoxycarbonyl)-amino]-acetic acid ethyl ester $^1$H NMR: (DMSO-D6, 400 MHz): 4.43 (2H, s), 6.73 (3H, d, J=8.8 Hz), 6.90-6.95 (4H, m), 7.57 (2H, d, J=8.4 Hz), 7.68 (2H, d, J=8.4 Hz), 7.83 (2H, s)

Example 121

[{3,5-Dichloro-4-[4-methoxy-3-(4-methyl-benzoyl)-phenoxy]-phenyl}-(4-methoxy-phenoxycarbonyl)-amino]-acetic acid ethyl ester $^1$H NMR: (CDCl$_3$, 400 MHz): 1.3 (3H, t, J=7.2 Hz), 2.36 (3H, s), 3.68 (3H, s), 4.27 (2H, s), 4.37-4.45 (2H, bs), 6.83-6.99 (5H, m), 7.03 (2H, d, J=8.0 Hz), 7.22 (2H, d, J=8.0 Hz), 7.49 (2H, s), 7.71 (2H, d, J=8.0 Hz)

Activity Data:

Invitro TR-α & TR-β activities were determined as per in-house protocols and the results of representative compounds are provided in tables 1 & 2 below as a proof of the efficacies of the novel class of compounds disclosed above.

TABLE 1

| Example No | EC$_{50}$ TR-α (nM) | EC$_{50}$ TR-β (nM) | EC$_{50}$ TR α/β |
|---|---|---|---|
| 1 | 440 | 146 | 3 |
| 2 | 118.9 | 161.90 | 0.73 |
| 3 | 274 | 89 | 3 |
| 23 | 9.26 | 2.6 | 3.56 |
| 26 | 176.3 | 28.1 | 6.27 |
| 44 | 84.83 | 14.83 | 5.72 |
| 47 | 16.4 | 11.3 | 1.45 |
| 49 | 38 | 10.3 | 3.68 |
| 50 | 23.3 | 6.2 | 3.76 |
| 55 | 106.78 | 64.3 | 1.66 |
| 56 | 13.4 | 20.4 | 0.65 |
| 63 | 337 | 254 | 1.33 |
| 67 | 49 | 12.8 | 3.82 |

TABLE 2

| Example | Conc. nM | TR-α * | TR-β * |
|---|---|---|---|
| 13 | 10 | 49.80 | 44.16 |
|  | 100 | 96.60 | 80.60 |
|  | 1000 | 72.90 | 75.00 |
| 14 | 10 | 11.10 | 16.40 |
|  | 100 | 36.30 | 58.50 |
|  | 1000 | 45.90 | 77.30 |
| 15 | 10 | 11.34 | 23.47 |
|  | 100 | 39.66 | 70.50 |
|  | 1000 | 33.74 | 66.77 |
| 17 | 10 | 21.19 | 27.69 |
|  | 100 | 51.82 | 72.82 |
|  | 1000 | 53.12 | 77.89 |
| 18 | 1 | 6.62 | 09.44 |
|  | 10 | 8.90 | 18.57 |
|  | 100 | 12.97 | 22.99 |
|  | 1000 | 16.87 | 42.59 |
| 20 | 1 | 10.42 | 19.94 |
|  | 10 | 15.74 | 40.69 |
|  | 100 | 21.47 | 87.72 |
|  | 1000 | 18.49 | 81.20 |
| 21 | 1 | 17.17 | 33.41 |
|  | 10 | 56.81 | 152.99 |
|  | 100 | 110.66 | 201.73 |
|  | 1000 | 93.53 | 147.91 |
| 24 | 1 | 10.00 | 20.00 |
|  | 10 | 20.00 | 40.00 |
|  | 100 | 50.00 | 100.0 |
|  | 1000 | 70.00 | 75.00 |
| 25 | 1 | 4.22 | 10.93 |
|  | 10 | 8.55 | 26.29 |
|  | 100 | 12.70 | 70.11 |
|  | 1000 | 7.15 | 51.67 |
| 28 | 1 | 8.97 | 10.36 |
|  | 10 | 14.71 | 20.94 |
|  | 100 | 25.77 | 45.43 |
|  | 1000 | 33.47 | 46.14 |
| 31 | 1 | 8.17 | 12.05 |
|  | 10 | 17.06 | 27.80 |
|  | 100 | 50.99 | 64.35 |
|  | 1000 | 46.21 | 75.23 |
| 32 | 1 | 23.36 | 24.67 |
|  | 10 | 74.20 | 73.68 |
|  | 100 | 87.50 | 118.67 |
|  | 1000 | 72.37 | 94.91 |
| 33 | 1 | 9.66 | 8.63 |
|  | 10 | 13.90 | 11.87 |
|  | 100 | 25.46 | 25.96 |
|  | 1000 | 46.33 | 46.76 |
| 34 | 1 | 12.66 | 08.37 |
|  | 10 | 26.23 | 21.27 |
|  | 100 | 62.95 | 51.14 |
|  | 1000 | 53.76 | 55.67 |
| 35 | 1 | 25.40 | 22.44 |
|  | 10 | 106.00 | 80.46 |
|  | 100 | 130.68 | 124.98 |
|  | 1000 | 72.06 | 81.27 |
| 37 | 1 | 14.93 | 21.20 |
|  | 10 | 40.84 | 66.73 |
|  | 100 | 71.78 | 124.67 |
|  | 1000 | 63.71 | 95.64 |
| 38 | 1 | 09.36 | 12.28 |
|  | 10 | 13.61 | 16.85 |
|  | 100 | 25.32 | 43.53 |
|  | 1000 | 41.59 | 81.37 |
| 41 | 1 | 20.78 | 23.34 |
|  | 10 | 56.19 | 73.45 |
|  | 100 | 99.00 | 89.96 |
|  | 1000 | 78.50 | 66.97 |
| 42 | 1 | 11.05 | 12.86 |
|  | 10 | 26.63 | 41.39 |
|  | 100 | 72.96 | 91.91 |
|  | 1000 | 80.89 | 86.01 |
| 45 | 1 | 10.48 | 13.47 |
|  | 10 | 12.02 | 18.73 |
|  | 100 | 23.05 | 47.09 |
|  | 1000 | 50.62 | 88.93 |
| 48 | 1 | 08.16 | 09.02 |
|  | 10 | 17.51 | 19.36 |
|  | 100 | 34.61 | 47.69 |
|  | 1000 | 45.08 | 37.61 |
| 51 | 1 | 08.05 | 08.68 |
|  | 10 | 14.43 | 16.98 |
|  | 100 | 32.52 | 54.59 |
|  | 1000 | 83.34 | 101.51 |
| 53 | 1 | 11.19 | 11.00 |
|  | 10 | 12.00 | 12.91 |
|  | 100 | 17.15 | 26.99 |
|  | 1000 | 50.30 | 91.71 |
| 57 | 1 | 21.61 | 12.61 |
|  | 10 | 24.62 | 14.81 |
|  | 100 | 35.93 | 23.62 |
|  | 1000 | 60.40 | 62.50 |
| 61 | 1 | 11.55 | 10.24 |
|  | 10 | 12.50 | 12.16 |
|  | 100 | 12.30 | 28.87 |
|  | 1000 | 28.11 | 85.19 |
| 66 | 1 | 20.56 | 36.67 |
|  | 10 | 15.36 | 25.90 |
|  | 100 | 18.11 | 40.67 |
|  | 1000 | 25.75 | 55.21 |

* Fold Induction w.r.t T3(100 nm)

The data above clearly indicates that several of the novel compounds of the present invention are selective to TR-beta receptor and therefore have potential therapeutically beneficial properties.

In-Vivo Studies:

Dose-response effects of T3 and selected compounds disclosed in the present invention on cholesterol lowering and change in heart rate in cholesterol-fed rats (treated for 7 days) was determined according to the general protocol described in PNAS, Aug. 19, 2003, vol. 100 (17) 10067-10072. Many of the compounds were found to be reducing cholesterol and having very little effect on the heart rate. Therefore, these compounds have the potential to be further developed as selective TR-beta agonists for the treatment of human and other animals in need of such treatment.

The novel compounds of the present invention may be formulated into suitable pharmaceutically acceptable compositions by combining with suitable excipients by techniques and processes and concentrations as are well known.

The compounds of formula (I) or pharmaceutical compositions containing them are useful as Thyroid hormone receptor ligands suitable for humans and other warm blooded animals, and may be administered either by oral, topical or parenteral administration for the treatment of various disease conditions associated with dyslipidemia, obesity etc.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:
1. A compound of formula (I) or a tautomer or pharmaceutically acceptable salt thereof

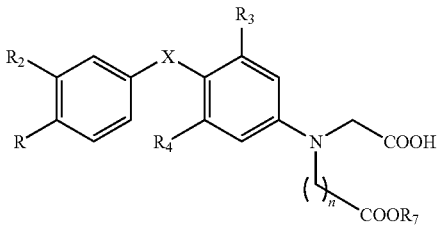

Formula (I)

wherein,
R is selected from $OR_1$, and $NHR_1$, wherein $R_1$ is selected from H, or an optionally substituted group selected from $(C_1-C_6)$alkyl, and $ar(C_1-C_6)$alkyl groups; $R_2$ represents hydrogen, hydroxyl, halo, or an optionally substituted group selected from $(C_1-C_6)$alkyl, acyl, oxo, $(C_3-C_7)$cycloalkyl, aryl, heteroaryl, alkoxy, aryloxy, aralkyl, aralkoxy, carboxylic acid and its derivatives selected from $(C_1-C_3)$alkyl esters and amides; sulfenyl derivatives, sulfonyl derivatives or a group —$CONR_5R_6$, or —$SO_2NR_5R_6$, wherein $R_5$ and $R_6$ are the same or different and are independently selected from H, or optionally substituted groups selected from $(C_1-C_6)$alkyl, $(C_3-C_7)$cycloalkyl, bicycloalkyl, aryl or $R_5$ and $R_6$ together with the nitrogen atom to which they are attached, form a five to eight membered cyclic ring which may optionally contain one or more additional hetero atoms selected from N, S, and O; $R_3$, and $R_4$ are same or different and are independently selected from H, halogen, or optionally substituted $(C_1-C_6)$alkyl groups; X is selected from O, —$CH_2$—, and CO; n represents 0 or 1; $R_7$ represents H, or an optionally substituted group selected from $(C_1-C_6)$alkyl, and aryl groups; with the provision that when n is 0, $R_7$ does not represent H.

2. The compound as claimed in claim 1, wherein $R_1$ is selected from H, or an optionally substituted group selected from $(C_1-C_3)$alkyl, and phenyl$(C_1-C_3)$alkyl groups; $R_2$ is selected from acyl, oxo groups or an optionally substituted group selected from $(C_1-C_6)$alkyl, phenyl, heteroaryl, benzyl, carboxylic acid and its derivatives selected from $(C_1-C_3)$alkyl esters and amides, or the groups —$CONR_5R_6$, and —$SO_2NR_5R_6$, wherein $R_5$ and $R_6$ may be same or different and are independently selected from H, or optionally substituted groups selected from $(C_1-C_6)$alkyl, $(C_3-C_7)$cycloalkyl, bicycloalkyl, phenyl or groups $R_5$ and $R_6$ together with the nitrogen atom to which they are attached, form a five to eight membered cyclic ring which may optionally contain one or more additional hetero atoms selected from N, and O; $R_3$, and $R_4$ are same or different and are independently selected from H, halogen, or optionally substituted $(C_1-C_6)$alkyl groups; X is selected from O, —$CH_2$—, and CO; n represents 0 or 1; $R_7$ represents H, or a optionally substituted group selected from $(C_1-C_6)$alkyl, and aryl groups; with the provision that when n is 0, $R_7$ does not represent H.

3. The compound as claimed in claim 1 wherein the substituents on $R_2$ are selected from hydroxy, halo, or optionally substituted groups selected from $(C_1-C_6)$alkyl, phenyl, and heteroaryl groups.

4. The compound as claimed in claim 1 wherein the substituents on alkyl, aryl, heteroaryl or cycloalkyl groups are selected from hydroxyl, halo, cyano, and optionally substituted groups selected from $(C_1-C_6)$alkyl, haloalkyl, alkoxy, oxo, aryl, aryloxy, aralkyl, acyl, alkylthio, and thioalkyl groups.

5. The compound as claimed in claim 1 selected from:
{[3,5-Dichloro-4-(4-hydroxy-3-isopropyl-phenoxy)-phenyl]-ethoxycarbonyl-amino}-acetic acid;
{[4-(3-sec-Butyl-4-hydroxy-phenoxy)-3,5-dichloro-phenyl]-ethoxycarbonyl-amino}-acetic acid;
{[4-(3-Benzyl-4-hydroxy-phenoxy)-3,5-dichloro-phenyl]-ethoxycarbonyl-amino}-acetic acid;
({4-[3-(Bicyclo[2.2.1]hept-2-ylcarbamoyl)-4-hydroxy-phenoxy]-3,5-dichloro-phenyl}-ethoxycarbonyl-amino)-acetic acid;
({3,5-Dichloro-4-[4-hydroxy-3-(piperidine-1-carbonyl)-phenoxy]-phenyl}-ethoxycarbonyl-amino)-acetic acid;
{[3,5-Dichloro-4-(3-ethyl-4-hydroxy-phenoxy)-phenyl]-ethoxycarbonyl-amino}-acetic acid;
{[3,5-Dichloro-4-(3-cyclohexylcarbamoyl-4-hydroxy-phenoxy)-phenyl]-ethoxycarbonyl-amino}-acetic acid;
({3,5-Dichloro-4-[4-hydroxy-3-(4-methyl-piperazine-1-carbonyl)-phenoxy]-phenyl}-ethoxycarbonyl-amino)-acetic acid;
{[3,5-Dichloro-4-(3-dimethylcarbamoyl-4-hydroxy-phenoxy)-phenyl]-ethoxycarbonyl-amino}-acetic acid;
{[3,5-Dichloro-4-(3-cyclobutylcarbamoyl-4-hydroxy-phenoxy)-phenyl]-ethoxycarbonyl-amino}-acetic acid;
{[3,5-Dichloro-4-(4-hydroxy-3-propyl-phenoxy)-phenyl]-ethoxycarbonyl-amino}-acetic acid;
{[3,5-Dichloro-4-(4-hydroxy-3-isopropylcarbamoyl-phenoxy)-phenyl]-ethoxycarbonyl-amino}-acetic acid;
{[4-(3-tert-Butyl-4-hydroxy-phenoxy)-3,5-dichloro-phenyl]-ethoxycarbonyl-amino}-acetic acid;
{[3,5-Dichloro-4-(6-hydroxy-biphenyl-3-yloxy)-phenyl]-ethoxycarbonyl-amino}-acetic acid;
({3,5-Dichloro-4-[3-(4-fluoro-benzoyl)-4-hydroxy-phenoxy]-phenyl}-ethoxycarbonyl-amino)-acetic acid;
{[3,5-Dichloro-4-(3-diethylcarbamoyl-4-hydroxy-phenoxy)-phenyl]-ethoxycarbonyl-amino}-acetic acid;
({3,5-Dichloro-4-[3-(5-chloro-thiophene-2-carbonyl)-4-hydroxy-phenoxy]-phenyl}-ethoxycarbonyl-amino)-acetic acid;
{[4-(3-sec-Butyl-4-hydroxy-phenoxy)-3,5-dimethyl-phenyl]-ethoxycarbonyl-amino}-acetic acid;
{[3,5-Dichloro-4-(4-hydroxy-3-phenylcarbamoyl-phenoxy)-phenyl]-ethoxycarbonyl-amino}-acetic acid;
({3,5-Dichloro-4-[3-(4-chloro-benzoyl)-4-hydroxy-phenoxy]-phenyl}-ethoxycarbonyl-amino)-acetic acid;
{[4-(3-sec-Butyl-4-hydroxy-phenoxy)-3,5-dimethyl-phenyl]-carboxymethyl-amino}-acetic acid;
({3,5-Dichloro-4-[3-(2,4-dichloro-benzoyl)-4-hydroxy-phenoxy]-phenyl}-ethoxycarbonyl-amino)-acetic acid;
[[4-(3-sec-Butyl-4-hydroxy-phenoxy)-3,5-dichloro-phenyl]-(4-hydroxy-phenoxycarbonyl)-amino]-acetic acid;
({4-[3-(4-tert-Butyl-benzoyl)-4-hydroxy-phenoxy]-3,5-dichloro-phenyl}-ethoxycarbonyl-amino)-acetic acid;
({3,5-Dichloro-4-[3-(3-chloro-benzoyl)-4-hydroxy-phenoxy]-phenyl}-ethoxycarbonyl-amino)-acetic acid;
{[4-(3-sec-Butyl-4-hydroxy-phenoxy)-3,5-dichloro-phenyl]-carboxymethyl-amino}-acetic acid;
({4-[3-(Bicyclo[2.2.1]hept-2-ylcarbamoyl)-4-hydroxy-phenoxy]-3,5-dichloro-phenyl}-carboxymethyl-amino)-acetic acid;
(Carboxymethyl-{3,5-dichloro-4-[3-(4-chloro-benzoyl)-4-hydroxy-phenoxy]-phenyl}-amino)-acetic acid;

(Carboxymethyl-{3,5-dichloro-4-[4-hydroxy-3-(piperidine-1-carbonyl)-phenoxy]-phenyl}-amino)-acetic acid;
({4-[3-(Bicyclo[2.2.1]hept-2-ylsulfamoyl)-4-hydroxy-phenoxy]-3,5-dichloro-phenyl}-carboxymethyl-amino)-acetic acid;
{Carboxymethyl-[3,5-dichloro-4-(4-hydroxy-3-isopropyl-phenoxy)-phenyl]-amino}-acetic acid;
[[3,5-Dichloro-4-(4-hydroxy-3-isopropyl-phenoxy)-phenyl]-(4-hydroxy-phenoxycarbonyl)-amino]-acetic acid;
(Carboxymethyl-{3,5-dichloro-4-[4-hydroxy-3-(piperidine-1-sulfonyl)-phenoxy]-phenyl}-amino)-acetic acid;
{[4-(3-tert-Butyl-4-hydroxy-phenoxy)-3,5-dichloro-phenyl]-carboxymethyl-amino}-acetic acid;
[[4-(3-tert-Butyl-4-hydroxy-phenoxy)-3,5-dichloro-phenyl]-(4-hydroxy-phenoxycarbonyl)-amino]-acetic acid;
{Carboxymethyl-[3,5-dichloro-4-(3-dimethylcarbamoyl-4-hydroxy-phenoxy phenyl]-amino}-acetic acid;
{Carboxymethyl-[4-(4-hydroxy-3-isopropyl-phenoxy)-3,5-dimethyl-phenyl]-amino}-acetic acid;
[[3,5-Dichloro-4-(3-dimethylsulfamoyl-4-hydroxy-phenoxy)-phenyl]-(4-hydroxy-phenoxycarbonyl)-amino]-acetic acid;
[[3,5-Dichloro-4-(3-dimethylcarbamoyl-4-hydroxy-phenoxy)-phenyl]-(4-hydroxy-phenoxycarbonyl)-amino]-acetic acid;
[{3,5-Dichloro-4-[4-hydroxy-3-(piperidine-1-carbonyl)-phenoxy]-phenyl}-(4-hydroxy-phenoxycarbonyl)-amino]-acetic acid;
[{3,5-Dichloro-4-[4-hydroxy-3-(piperidine-1-sulfonyl)-phenoxy]-phenyl}-(4-hydroxy-phenoxycarbonyl)-amino]-acetic acid;
[[4-(4-Hydroxy-3-isopropyl-phenoxy)-3,5-dimethyl-phenyl]-(4-hydroxy phenoxycarbonyl)-amino]-acetic acid;
[{4-[3-(4-tert-Butyl-benzoyl)-4-hydroxy-phenoxy]-3,5-dichloro-phenyl}-(4-hydroxy-phenoxycarbonyl)-amino]-acetic acid;
[{3,5-Dichloro-4-[3-(4-chloro-benzoyl)-4-hydroxy-phenoxy]-phenyl}-(4-hydroxy-phenoxycarbonyl)-amino]-acetic acid;
[[3,5-Dichloro-4-(4-hydroxy-3-isopropylsulfamoyl-phenoxy)-phenyl]-(4-hydroxy-phenoxycarbonyl)-amino]-acetic acid;
{Carboxymethyl-[3,5-dichloro-4-(3-ethyl-4-hydroxy-phenoxy)-phenyl]-amino}-acetic acid;
[{3,5-Dichloro-4-[3-(3-chloro-benzoyl)-4-hydroxy-phenoxy]-phenyl}-(4-hydroxy-phenoxycarbonyl)-amino]-acetic acid;
[[3,5-Dichloro-4-(3-ethyl-4-hydroxy-phenoxy)-phenyl]-(4-hydroxy-phenoxycarbonyl)-amino]-acetic acid;
[[3,5-Dichloro-4-(6-hydroxy-biphenyl-3-yloxy)-phenyl]-(4-hydroxy-phenoxycarbonyl)-amino]-acetic acid;
[[4-(3-Benzyl-4-hydroxy-phenoxy)-3,5-dichloro-phenyl]-(4-hydroxy-phenoxycarbonyl)-amino]-acetic acid;
[[3,5-Dichloro-4-(3-cyclobutylsulfamoyl-4-hydroxy-phenoxy)-phenyl]-(4-hydroxy-phenoxycarbonyl)-amino]-acetic acid;
[{4-[3-(Bicyclo[2.2.1]hept-2-ylsulfamoyl)-4-hydroxy-phenoxy]-3,5-dichloro-phenyl}-(4-hydroxy-phenoxycarbonyl)-amino]-acetic acid;
[{4-[3-(Bicyclo[2.2.1]hept-2-ylsulfamoyl)-4-hydroxy-phenoxy]-3,5-dibromo-phenyl}-(4-hydroxy-phenoxycarbonyl)-amino]-acetic acid;
[{3,5-Dichloro-4-[4-hydroxy-3-(4 hydroxy-benzoyl)-phenoxy]-phenyl}-(4-hydroxy-phenoxycarbonyl)-amino]-acetic acid;
[{3,5-Dichloro-4-[3-(4-fluoro-benzoyl)-4-hydroxy-phenoxy]-phenyl}-(4-hydroxy-phenoxycarbonyl)-amino]-acetic acid;
[(3,5-Dichloro-4-{3-[(4-chloro-phenyl)-hydroxy-methyl]-4-hydroxy-phenoxy}-phenyl)-(4-hydroxy-phenoxycarbonyl)-amino]-acetic acid;
[{4-[3-(Azepane-1-sulfonyl)-4-hydroxy-phenoxy]-3,5-dichloro-phenyl}-(4-hydroxy-phenoxycarbonyl)-amino]-acetic acid;
({3,5-Dichloro-4-[3-(1-ethyl-propoxy)-4-hydroxy-phenoxy]-phenyl}-ethoxycarbonyl-amino)-acetic acid;
[[4-(3-sec-Butyl-4-hydroxy-phenoxy)-3,5-dimethyl-phenyl]-(4-hydroxy-phenoxycarbonyl)-amino]-acetic acid;
[[3,5-Dichloro-4-(3-cyclohexylsulfamoyl-4-hydroxy-phenoxy)-phenyl]-(4-hydroxy-phenoxycarbonyl)-amino]-acetic acid;
[{3,5-Dichloro-4-[4-hydroxy-3-(morpholine-4-sulfonyl)-phenoxy]-phenyl}-(4-hydroxy-phenoxycarbonyl)-amino]-acetic acid;
({3,5-Dichloro-4-[4-hydroxy-3-(3-methyl-benzoyl)-phenoxy]-phenyl}-ethoxycarbonyl-amino)-acetic acid;
[{3,5-Dichloro-4-[4-hydroxy-3-(pyrrolidine-1-sulfonyl)-phenoxy]-phenyl}-(4-hydroxy-phenoxycarbonyl)-amino]-acetic acid;
{[3,5-Dichloro-4-(4-hydroxy-3-isobutoxy-phenoxy)-phenyl]-ethoxycarbonyl-amino}-acetic acid;
{[3,5-Dichloro-4-(3-cyclohexylmethoxy-4-hydroxy-phenoxy)-phenyl]-ethoxycarbonyl-amino}-acetic acid;
[{3,5-Dichloro-4-[4-hydroxy-3-(3-methyl-benzoyl)-phenoxy]-phenyl}-(4-hydroxy-phenoxycarbonyl)-amino]-acetic acid;
[{3,5-Dibromo-4-[3-(4-chloro-benzoyl)-4-hydroxy-phenoxy]-phenyl}-(4-hydroxy-phenoxycarbonyl)-amino]-acetic acid;
({3,5-Dibromo-4-[3-(4-chloro-benzoyl)-4-hydroxy-phenoxy]-phenyl}-ethoxycarbonyl-amino)-acetic acid;
({3,5-Dichloro-4-[4-hydroxy-3-(4-methyl-benzoyl)-phenoxy]-phenyl}-ethoxycarbonyl-amino)-acetic acid;
[{3,5-Dichloro-4-[4-hydroxy-3-(4-methyl-benzoyl)-phenoxy]-phenyl}-(4-hydroxy-phenoxycarbonyl)-amino]-acetic acid;
{[3,5-Dichloro-4-(3-isopropyl-4-methoxy-phenoxy)-phenyl]-ethoxycarbonyl-amino}-acetic acid ethyl ester;
{[4-(4-Benzyloxy-3-isopropyl-phenoxy)-3,5-dichloro-phenyl]-ethoxycarbonyl-amino}-acetic acid ethyl ester;
{[4-(3-sec-Butyl-4-methoxy-phenoxy)-3,5-dichloro-phenyl]-ethoxycarbonyl-amino}-acetic acid ethyl ester;
{[4-(3-Benzyl-4-methoxy-phenoxy)-3,5-dichloro-phenyl]-ethoxycarbonyl-amino}-acetic acid ethyl ester;
({4-[3-(Bicyclo[2.2.1]hept-2-ylcarbamoyl)-4-methoxy-phenoxy]-3,5-dichloro-phenyl}-ethoxycarbonyl-amino)-acetic acid ethyl ester;
({3,5-Dichloro-4-[4-methoxy-3-(piperidine-1-carbonyl)-phenoxy]-phenyl}-ethoxycarbonyl-amino)-acetic acid ethyl ester;
{[3,5-Dichloro-4-(3-ethyl-4-methoxy-phenoxy)-phenyl]-ethoxycarbonyl-amino}-acetic acid ethyl ester;
{[3,5-Dichloro-4-(3-cyclohexylcarbamoyl-4-methoxy-phenoxy)-phenyl]-ethoxycarbonyl-amino}-acetic acid ethyl ester;
({3,5-Dichloro-4-[4-methoxy-3-(4-methyl-piperazine-1-carbonyl)-phenoxy]-phenyl}-ethoxycarbonyl-amino)-acetic acid ethyl ester;
{[3,5-Dichloro-4-(3-dimethylcarbamoyl-4-methoxy-phenoxy)-phenyl]-ethoxycarbonyl-amino}-acetic acid ethyl ester;

{[3,5-Dichloro-4-(3-cyclobutylcarbamoyl-4-methoxy-phenoxy)-phenyl]-ethoxycarbonyl-amino}-acetic acid ethyl ester;

{[3,5-Dichloro-4-(4-methoxy-3-propyl-phenoxy)-phenyl]-ethoxycarbonyl-amino}-acetic acid ethyl ester;

{[3,5-Dichloro-4-(3-isopropylcarbamoyl-4-methoxy-phenoxy)-phenyl]-ethoxycarbonyl-amino}-acetic acid ethyl ester;

{[4-(3-tert-Butyl-4-methoxy-phenoxy)-3,5-dichloro-phenyl]-ethoxycarbonyl-amino}-acetic acid ethyl ester;

{[3,5-Dichloro-4-(6-methoxy-biphenyl-3-yloxy)-phenyl]-ethoxycarbonyl-amino}-acetic acid ethyl ester;

({3,5-Dichloro-4-[3-(4-fluoro-benzoyl)-4-methoxy-phenoxy]-phenyl}-ethoxycarbonyl-amino)-acetic acid ethyl ester;

{[3,5-Dichloro-4-(3-diethylcarbamoyl-4-methoxy-phenoxy)-phenyl]-ethoxycarbonyl-amino}-acetic acid ethyl ester;

({3,5-Dichloro-4-[3-(5-chloro-thiophene-2-carbonyl)-4-methoxy-phenoxy]-phenyl}-ethoxycarbonyl-amino)-acetic acid ethyl ester;

{[4-(3-sec-Butyl-4-methoxy-phenoxy)-3,5-dimethyl-phenyl]-ethoxycarbonyl-amino}-acetic acid ethyl ester;

{[3,5-Dichloro-4-(4-methoxy-3-phenylcarbamoyl-phenoxy)-phenyl]ethoxycarbonyl-amino}-acetic acid ethyl ester;

({3,5-Dichloro-4-[3-(4-chloro-benzoyl)-4-methoxy-phenoxy]-phenyl}-ethoxycarbonyl-amino)-acetic acid ethyl ester;

{[4-(3-sec-Butyl-4-methoxy-phenoxy)-3,5-dimethyl-phenyl]ethoxycarbonylmethyl-amino}-acetic acid ethyl ester;

({3,5-Dichloro-4-[3-(2,4-dichloro-benzoyl)-4-methoxy-phenoxy]-phenyl}-ethoxycarbonyl-amino)-acetic acid ethyl ester;

[[4-(3-sec-Butyl-4-methoxy-phenoxy)-3,5-dichloro-phenyl]-(4-methoxy-phenoxycarbonyl)-amino]-acetic acid ethyl ester;

({4-[3-(4-tert-Butyl-benzoyl)-4-methoxy-phenoxy]-3,5-dichloro-phenyl}-ethoxycarbonyl-amino)-acetic acid ethyl ester;

({3,5-Dichloro-4-[3-(3-chloro-benzoyl)-4-methoxy-phenoxy]-phenyl}-ethoxycarbonyl-amino)-acetic acid ethyl ester;

{[4-(3-sec-Butyl-4-methoxy-phenoxy)-3,5-dichloro-phenyl]-ethoxycarbonylmethyl-amino}-acetic acid ethyl ester;

({4-[3-(Bicyclo[2.2.1]hept-2-ylcarbamoyl)-4-methoxy-phenoxy]-3,5-dichloro-phenyl}-ethoxycarbonylmethyl-amino)-acetic acid ethyl ester;

({3,5-Dichloro-4-[3-(4-chloro-benzoyl)-4-methoxy-phenoxy]-phenyl}-ethoxycarbonylmethyl-amino)-acetic acid ethyl ester;

({3,5-Dichloro-4-[4-methoxy-3-(piperidine-1-carbonyl)-phenoxy]-phenyl}-ethoxycarbonylmethyl-amino)-acetic acid ethyl ester;

({4-[3-(Bicyclo[2.2.1]hept-2-ylsulfamoyl)-4-methoxy-phenoxy]-3,5-dichloro-phenyl}-ethoxycarbonylmethyl-amino)-acetic acid ethyl ester;

{[3,5-Dichloro-4-(3-isopropyl-4-methoxy-phenoxy)-phenyl]-ethoxycarbonylmethyl-amino}-acetic acid ethyl ester;

[[3,5-Dichloro-4-(3-isopropyl-4-methoxy-phenoxy)-phenyl]-(4-methoxy-phenoxycarbonyl)-amino]acetic acid ethyl ester;

({3,5-Dichloro-4-[4-methoxy-3-(piperidine-1-sulfonyl)-phenoxy]-phenyl}-ethoxycarbonylmethyl-amino)-acetic acid ethyl ester;

{[4-(3-tert-Butyl-4-methoxy-phenoxy)-3,5-dichloro-phenyl]-ethoxycarbonylmethyl-amino}-acetic acid ethyl ester;

[[4-(3-tert-Butyl-4-methoxy-phenoxy)-3,5-di chloro-phenyl]-(4-methoxy-phenoxycarbonyl)-amino]acetic acid ethyl ester;

{[3,5-Dichloro-4-(3-dimethylcarbamoyl-4-methoxy-phenoxy)-phenyl]-ethoxycarbonylmethyl-amino}-acetic acid ethyl ester;

{Ethoxycarbonylmethyl-[4-(3-isopropyl-4-methoxy-phenoxy)-3,5-dimethyl-phenyl]-amino}-acetic acid ethyl ester;

[[3,5-Dichloro-4-(3-dimethylsulfamoyl-4-methoxy-phenoxy)-phenyl]-(4-methoxy-phenoxycarbonyl)-amino]-acetic acid ethyl ester;

[[3,5-Dichloro-4-(3-dimethylcarbamoyl-4-methoxy-phenoxy)-phenyl]-(4-methoxy-phenoxycarbonyl)-amino]-acid ethyl ester;

[{3,5-Dichloro-4-[4-methoxy-3-(piperidine-1-carbonyl)-phenoxy]-phenyl}-(4-methoxy-phenoxycarbonyl)-amino]-acetic acid ethyl ester;

[{3,5-Dichloro-4-[4-methoxy-3-(piperidine-1-sulfonyl)-phenoxy]-phenyl}-(4-methoxy-phenoxycarbonyl)-amino]acetic acid ethyl ester;

[[4-(3-Isopropyl-4-methoxy-phenoxy)-3,5-dimethyl-phenyl]-(4-methoxy-phenoxycarbonyl)-amino]-acetic acid ethyl ester;

[{4-[3-(4-tert-Butyl-benzoyl)-4-methoxy-phenoxy]-3,5-dichloro-phenyl}-(4-methoxy-phenoxycarbonyl)-amino]-acetic acid ethyl ester;

[{3,5-Dichloro-4-[3-(4-chloro-benzoyl)-4-methoxy-phenoxy]-phenyl}-(4-methoxy-phenoxycarbonyl)-amino]-acetic acid ethyl ester;

[[3,5-Dichloro-4-(3-isopropylsulfamoyl-4-methoxy-phenoxy)-phenyl]-(4-methoxy-phenoxycarbonyl)-amino]acetic acid ethyl ester;

{[3,5-Dichloro-4-(3-ethyl-4-methoxy-phenoxy)-phenyl]-ethoxycarbonylmethyl-amino}-acetic acid ethyl ester;

[{3,5-Dichloro-4-[3-(3-chloro-benzoyl)-4-methoxy-phenoxy]-phenyl}-(4-methoxy-phenoxycarbonyl)-amino]-acetic acid ethyl ester;

[[3,5-Dichloro-4-(3-ethyl-4-methoxy-phenoxy)-phenyl]-(4-methoxy-phenoxycarbonyl)-amino]-acetic acid ethyl ester;

[[3,5-Dichloro-4-(6-methoxy-biphenyl-3-yloxy)-phenyl]-(4-methoxy-phenoxycarbonyl)-amino]-acetic acid ethyl ester;

[[4-(3-Benzyl-4-methoxy-phenoxy)-3,5-dichloro-phenyl]-(4-methoxy-phenoxycarbonyl)-amino]-acetic acid ethyl ester;

[[3,5-Dichloro-4-(3-cyclobutylsulfamoyl-4-methoxy-phenoxy)-phenyl]-(4-methoxy-phenoxycarbonyl)-amino]-acetic acid ethyl ester;

[{4-[3-(Bicyclo[2.2.1]hept-2-ylsulfamoyl)-4-methoxy-phenoxy]-3,5-dichloro-phenyl}-(4-methoxy-phenoxycarbonyl)-amino]-acetic acid ethyl ester;

[{4-[3-(Bicyclo[2.2.1]hept-2-ylsulfamoyl)-4-methoxy-phenoxy]-3,5-dibromo-phenyl}-(4-methoxy-phenoxycarbonyl)-amino]-acetic acid ethyl ester;

[{3,5-Dichloro-4-[4-methoxy-3-(4-methoxy-benzoyl)-phenoxy]-phenyl}-(4-methoxy-phenoxycarbonyl)-amino]-acetic acid ethyl ester;

[{3,5-Dichloro-4-[3-(4-fluoro-benzoyl)-4-methoxy-phenoxy]-phenyl}-(4-methoxy-phenoxycarbonyl)-amino]-acetic acid ethyl ester;

[{4-[3-(Azepane-1-sulfonyl)-4-methoxy-phenoxy]-3,5-dichloro-phenyl}-(4-methoxy-phenoxycarbonyl)-amino]-acetic acid ethyl ester;

({4-[4-Benzyloxy-3-(1-ethyl-propoxy)-phenoxy]-3,5-dichloro-phenyl}-ethoxycarbonyl-amino)-acetic acid ethyl ester;

[[4-(3-sec-Butyl-4-methoxy-phenoxy)-3,5-dimethyl phenyl]-(4-methoxy-phenoxycarbonyl)-amino]-acetic acid ethyl ester;

[[3,5-Dichloro-4-(3-cyclohexylsulfamoyl-4-methoxy-phenoxy)-phenyl]-(4-methoxy-phenoxycarbonyl)-amino]-acetic acid ethyl ester;

[{3,5-Dichloro-4-[4-methoxy-3-(morpholine-4-sulfonyl)-phenoxy]-phenyl}-(4-methoxy-phenoxycarbonyl)-amino]-acetic acid ethyl ester;

({3,5-Dichloro-4-[4-methoxy-3-(3-methyl-benzoyl)-phenoxy]-phenyl}-ethoxycarbonyl-amino)-acetic acid ethyl ester;

[{3,5-Dichloro-4-[4-methoxy-3-(pyrrolidine-1-sulfonyl)-phenoxy]-phenyl}-(4-methoxy-phenoxycarbonyl)-amino]-acetic acid ethyl ester;

{[4-(4-Benzyloxy-3-isobutoxy-phenoxy)-3,5-dichloro-phenyl]-ethoxycarbonyl-amino}-acetic acid ethyl ester;

{[4-(4-Benzyloxy-3-cyclohexylmethoxy-phenoxy)-3,5-dichloro-phenyl]-ethoxycarbonyl-amino}-acetic acid ethyl ester;

[{3,5-Dichloro-4-[4-methoxy-3-(3-methyl-benzoyl)-phenoxy]-phenyl}-(4-methoxy-phenoxycarbonyl)-amino]-acetic acid ethyl ester;

[{3,5-Dibromo-4-[3-(4-chloro-benzoyl)-4-methoxy-phenoxy]-phenyl}-(4-methoxy-phenoxycarbonyl)-amino]-acetic acid ethyl ester;

({3,5-Dibromo-4-[3-(4-chloro-benzoyl)-4-methoxy-phenoxy]-phenyl}-ethoxycarbonyl-amino)-acetic acid ethyl ester;

({3,5-Dichloro-4-[4-methoxy-3-(4-methyl-benzoyl)-phenoxy]-phenyl}-ethoxycarbonyl-amino)-acetic acid ethyl ester; and

[{3,5-Dichloro-4-[4-methoxy-3-(4-methyl-benzoyl)-phenoxy]-phenyl}-(4-methoxy-phenoxycarbonyl)-amino]-acetic acid ethyl ester.

6. A pharmaceutical composition which comprises compound as claimed in claim 1 and at least one pharmaceutically acceptable carrier, diluent or excipient.

7. A pharmaceutical composition which comprises a compound of formula (I), as claimed in claim 2 and at least one pharmaceutically acceptable carrier, diluent or excipient.

8. A pharmaceutical composition which comprises a compound of formula (I), as claimed in claim 3 and at least one pharmaceutically acceptable carrier, diluent or excipient.

9. A pharmaceutical composition which comprises a compound of formula (I), as claimed in claim 4 and at least one pharmaceutically acceptable carrier, diluent or excipient.

10. A pharmaceutical composition which comprises a compound of formula (I), as claimed in claim 5 and at least one pharmaceutically acceptable carrier, diluent or excipient.

\* \* \* \* \*